(12) United States Patent
Brown et al.

(10) Patent No.: US 6,844,362 B2
(45) Date of Patent: Jan. 18, 2005

(54) INDOLE DERIVATIVES USEFUL FOR THE TREATMENT OF DISEASES

(75) Inventors: Alan Daniel Brown, Kent (GB); Justin Stephen Bryans, Kent (GB); Mark Edward Bunnage, Kent (GB); Paul Alan Glossop, Kent (GB); Charlotte Alice Louise Lane, Kent (GB); Russell Andrew Lewthwaite, Kent (GB); Simon Mantell, Kent (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/684,233

(22) Filed: Oct. 9, 2003

(65) Prior Publication Data

US 2004/0116503 A1 Jun. 17, 2004

Related U.S. Application Data

(60) Provisional application No. 60/438,639, filed on Jan. 8, 2003.

(30) Foreign Application Priority Data

Oct. 11, 2002 (EP) .............................................. 02292513
Jan. 10, 2003 (EP) .............................................. 03290069

(51) Int. Cl.$^7$ ..................... A61K 31/404; C07D 209/04
(52) U.S. Cl. ....................................... 514/419; 548/491
(58) Field of Search ........................... 548/491; 514/419

(56) References Cited

U.S. PATENT DOCUMENTS

| 3,699,123 A | * | 10/1972 | Seemann et al. ............ 548/492 |
| 5,030,640 A | * | 7/1991 | Fisher et al. ................. 514/339 |
| 2002/0128290 A1 | | 9/2002 | Ohshima et al. ............. 514/336 |

FOREIGN PATENT DOCUMENTS

| EP | 0801060 | 10/1997 | ......... C07D/209/42 |
| EP | 0822185 | 2/1998 | ......... C07D/209/42 |
| WO | WO9429290 | 12/1994 | ......... C07D/307/85 |
| WO | WO0142193 | 6/2001 | ......... C07C/233/43 |

* cited by examiner

*Primary Examiner*—Golam M M Shameem
(74) *Attorney, Agent, or Firm*—Peter C. Richardson; Gregg C. Benson; Robert T. Ronau

(57) ABSTRACT

The invention relates to indole derivatives and to processes for the preparation of, intermediates used in the preparation of, compositions containing and the uses of, such derivatives. The indole derivatives according to the present invention are useful in numerous diseases, disorders and conditions, in particular inflammatory, allergic and respiratory diseases, disorders and conditions.

11 Claims, No Drawings

INDOLE DERIVATIVES USEFUL FOR THE TREATMENT OF DISEASES

This invention relates to β2 agonists of the indole derivatives family of general formula:

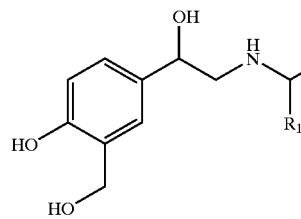

(1)

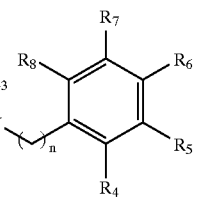

in which $R_1$, $R_2$, $R_3$, $R_4$, $R_5$, $R_6$, $R_7$, $R_8$ and n have the meanings indicated below, and to processes for the preparation of, intermediates used in the preparation of, compositions containing and the uses of, such derivatives.

Adrenoceptors are members of the large G-protein coupled receptor super-family. The adrenoceptor subfamily is itself divided into the α and β subfamilies with the β sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S–26S and Bryan, S. A. et al, Expert Opinion on investigational drugs, 2000, 9:1, pp25–42) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, β2 agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel β2 agonists that would have an appropriate pharmacological profile, for example in terms of potency. In this context, the present invention relates to novel β2 agonists of the indole derivatives family.

Various indole derivatives have already been synthesised. For example, the patent application EP 801 060 discloses dihydroindole derivatives having a selective β3 agonist activity, of formula

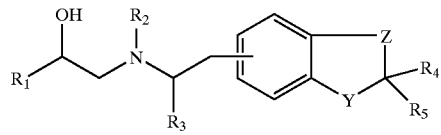

wherein $R_1$ may be an optionally substituted phenyl (1 to 3 substitutents which may be selected from hydroxyl and hydroxyalkyl), $R_2$ may be hydrogen, $R_3$ is hydrogen or alkyl, Z is —$CH_2$— or —$CH_2$—$CH_2$—, Y may be —$NR_7$— ($R_7$ may be hydrogen and alkyl) and $R_4$ and $R_5$ are independently hydrogen, $COOR_6$, $COONR_6R_6$, CHO, $COR_6$, $CH_2OH$, $CH_2OCH_2COOR_6$ and $CH_2OCH_2CH_2OR_6$ ($R_6$ is hydrogen or alkyl).

Another example concerns the patent application EP 822 185 that also discloses selective β3 agonists of formula:

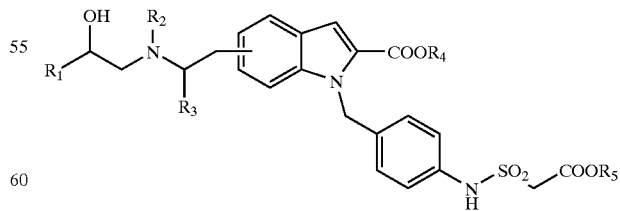

wherein $R_1$ may be an optionally substituted phenyl with 1 to 3 substitutents selected from hydroxy and hydroxyalkyl, $R_2$ may be hydrogen, and $R_3$ may be hydrogen or alkyl optionally independently substituted with one or more halo atoms.

However, none of the indole derivatives synthetised so far have shown β2 agonist activity with high potency (they are all selective β3 agonists) allowing them to be used as efficient drugs in the treatment of the β2-mediated diseases and/or conditions, in particular allergic and non-allergic airways diseases.

It has now been found that the new indole derivatives of general formula (1):

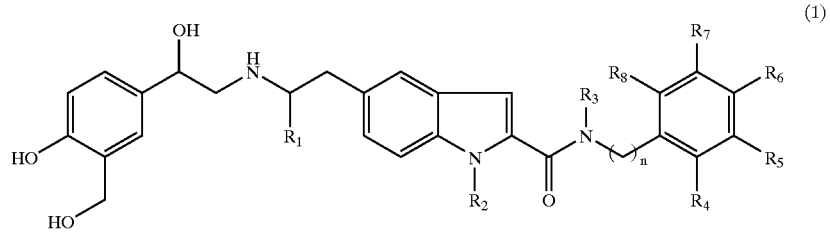

(1)

wherein
n is an integer equal to 0, 1, 2, 3 or 4;
$R_1$ and $R_2$ are each independently selected from hydrogen and $(C_1-C_4)$alkyl;
$R_3$ is selected from the group consisting of hydrogen or $(C_1-C_6)$alkyl optionally substituted by a hydroxy; and
$R_4$, $R_5$, $R_6$, $R_7$ and $R_8$ are each independently selected from the group consisting of hydrogen, hydroxy, $(C_1-C_6)$alkyl, $(C_1-C_6)$alkoxy, benzyloxy, hydroxy$(C_1-C_6)$alkyl, thio$(C_1-C_6)$alkyl, halo and trifluoromethyl,
or, if appropriate, their pharmaceutically acceptable salts and/or isomers, tautomers, solvates or isotopic variations thereof,
are agonists of the β2 receptors, that are particularly useful for the treatment of β2-mediated diseases and/or conditions, by showing good potency, in particular when administered via the inhalation route.

In the present invention, the term "potent" means that the compounds of formula (1) show an agonist potency for the β2 receptor, which is less than 10 nM as measured by the cell-based assay described herein.

In the here above general formula (1), $(C_1-C_4)$ radicals denote a straight-chain or branched group containing 1, 2, 3 or 4 carbon atoms and $(C_1-C_6)$alkyl radicals denote a straight-chain or branched group containing 1, 2, 3, 4, 5 or 6 carbon atoms respectively. This also applies if they carry substituents or occur as substituents of other radicals, for example in $(C_1-C_6)$alkoxy radicals, hydroxy$(C_1-C_6)$alkyl radicals, thio$(C_1-C_6)$alkyl radicals etc. . . . Examples of suitable $(C_1-C_6)$alkyl radicals are methyl, ethyl, n-propyl, iso-propyl, n-butyl, iso-butyl, sec-butyl, tert-butyl, n-pentyl, iso-pentyl, tert-pentyl, n-hexyl, iso-hexyl, 3-methylpentyl etc. . . . Examples of suitable $(C_1-C_6)$alkoxy radicals are methoxy, ethoxy, n-propyloxy, iso-propyloxy, n-butyloxy, iso-butyloxy, sec-butyloxy and tert-butyloxy, n-pentyloxy, iso-pentyloxy, tert-pentyloxy, n-hexyloxy, iso-hexyloxy, 3-methylpentyloxy etc. . . . Hydroxy$(C_1-C_6)$alkyl radicals are alkyl radicals substituted by a hydroxy group (—OH). According to a preferred embodiment of said invention, such radicals contain one hydroxy substituent. Examples of suitable hydroxy$(C_1-C_6)$alkyl radicals are hydroxymethyl, 1-hydroxyethyl or 2-hydroxyethyl. Thio$(C_1-C_6)$alkyl radicals are alkyl radicals attached to through a —S— atom, i.e. thio$(C_1-C_6)$alkyl means —S-alkyl. Examples of suitable thio$(C_1-C_6)$alkyl radicals are thiomethyl, thioethyl, thiopropyl etc. . . .

In the general formula (1) according to the present invention, when a radical is mono- or poly-substituted, said substituent(s) can be located at any desired position(s). Also, when a radical is polysubstituted, said substituents can be identical or different.

Finally, halo denotes a halogen atom selected from the group consisting of fluoro, chloro, bromo and iodo in particular fluoro or chloro.

The indole derivatives of the formula (1) can be prepared using conventional procedures such as by the following illustrative methods in which $R_1$ to $R_8$ and n are as previously defined for the indole derivatives of the formula (1) unless otherwise stated.

The indole derivatives of the formula (1) may be prepared by coupling an acid of formula (2):

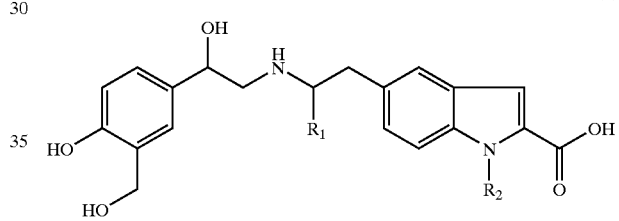

(2)

with an amine of formula (3):

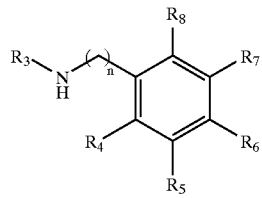

(3)

wherein n and $R_1$ to $R_8$ are as previously defined. The coupling is generally carried out in an excess of said amine as an acid receptor, with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or diisopropylethylamine). The reaction may be undertaken in a suitable solvent such as pyridine, dimethylformamide, tetrahydrofuran, dimethylsulfoxide, dichloromethane or ethyl acetate, and at temperature comprised between 10° C. and 40° C. (room temperature). It may also be necessary to further manipulate a structure of compound of formula (1) to yield another desired compound of formula (1). For example, to yield a hydroxy substituent from a benzyloxy substituent, a hydrogenation reaction can be performed typically at 15–60 psi in a solvent such as methanol or ethanol at ambient or up to 50° C.

Said amine (3) is either commercially available or may be prepared by conventional methods well known to the one skilled in the art (e.g. reduction, oxidation, alkylation, protection, deprotection etc. . . . ) from commercially available material.

The acid of formula (2) may be prepared from the corresponding ester of formula (4):

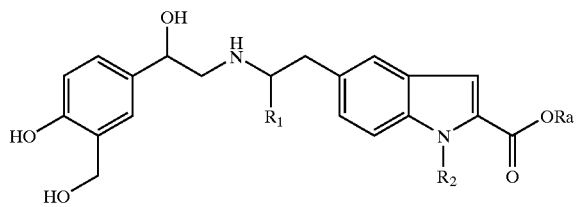

(4)

wherein Ra is a suitable acid protecting group, preferably a $(C_1-C_4)$alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

The ester of formula (4) may be prepared by reaction of an amine of formula (5):

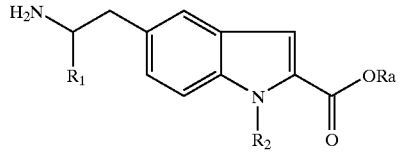

(5)

wherein Ra is as previously defined,
with a bromide of formula (6):

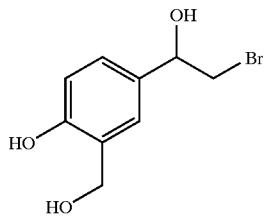

(6)

In a typical procedure, the amine of formula (5) is reacted with a bromide of formula (6) optionally in the presence of a solvent or mixture of solvents (e.g. dimethyl sulphoxide, toluene, N,N-dimethylformamide), optionally in the presence of a suitable base (e.g. triethylamine, diisopropylethylamine) at a temperature comprised between 80° C. and 120° C., for 12 to 48 hours.

The bromide of formula (6) may be prepared from the ester of formula (7):

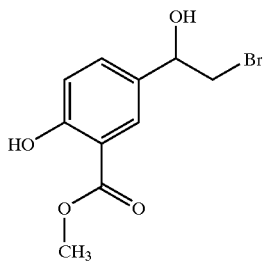

(7)

according to any method well-known to the one skilled in the art to prepare an alcohol from an ester, without modifying the rest of the molecule.

In a typical procedure, the ester of formula (7) is reduced with borane methylsulfide complex in tetrahydrofuran at a reflux for a period of 2 hours.

The alcohol of formula (7) may be prepared as either the (R) or (S) enantiomer according to methods well described in the literature (Tetrahedron Letters 1994, 35(50), 9375).

The amine of formula (5) may be prepared as either the (R) or (S) enantiomer from the corresponding protected indole of formula (8):

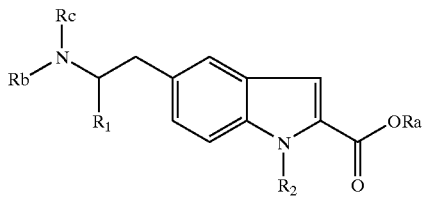

(8)

wherein Ra is as previously defined and Rb and Rc represent any suitable substituents so that HNRbRc is a chiral amine (for example, Rb may be hydrogen and Rc may be a α-methylbenzyl group), provided that the bonds between N and Rb and N and Rc can be easily cleaved to give the free amine of formula (5) using standard methodology for cleaving nitrogen protecting groups, such as that found in the text book (see for example T. W. GREENE, Protective Groups in Organic Synthesis, A. Wiley-Interscience Publication, 1981).

The amine of formula (8) as a single diastereomer may be prepared by alkylation of a compound of formula (9):

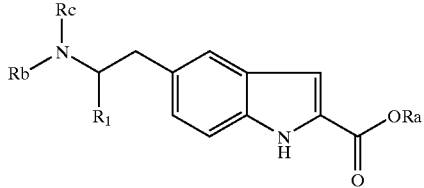

(9)

wherein $R_1$, Ra, Rb and Rc are as previously defined.

In a typical procedure, the compound of formula (9) may be alkylated with a suitable alkylating agent (e.g. $R_2Br$ or $R_2I$) in the presence of a suitable base (e.g. sodium hydride). The reaction is generally done in a solvent such as tetrahydrofuran or dimethylformamide, at a temperature comprised between -10° C. and 80° C. for 1 to 16 hours. The product is then converted to the hydrochloride salt and selectively crystallised from a suitable solvent or mixture of solvents (e.g. isopropanol, ethanol, methanol, diisopropyl ether or diisopropyl ether/methanol) to give the chiral product of formula (8) or its enantiomer if the opposite enantiomer of the amine NHRbRc is used.

The compound of formula (9) may be prepared by reaction of an amine of formula HNRbRc with a ketone of formula (10):

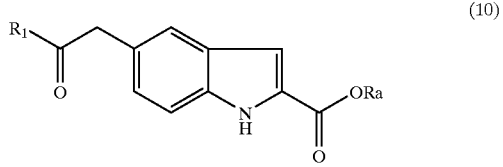

wherein $R_1$, Ra, Rb and Rc are as previously defined.

In a typical procedure, the reaction of the ketone of formula (10) with the amine of formula HNRbRc leads to a chiral intermediate which is in turn reduced by a suitable reducing agent (e.g. sodium cyanoborohydride of formula $NaCNBH_3$ or sodium triacetoxyborohydride of formula $Na(OAc)_3BH$) optionally in the presence of a drying agent (e.g. molecular sieves, magnesium sulfate) and optionally in the presence of an acid catalyst (e.g. acetic acid) to give the amine of formula (9). The reaction is generally done in a solvent such as tetrahydrofuran or dichloromethane at a temperature comprised between 20° C. and 80° C. for 3 to 72 hours.

The ketone of formula (10) may be prepared by palladium mediated coupling of an aryl halide of formula (11):

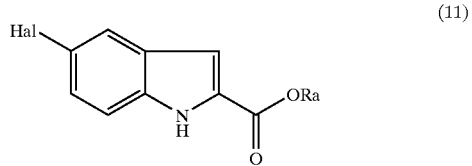

wherein Ra is as previously defined and Hal represents an halogen atom, which includes, but is not limited to bromo and iodo, with an enolate or enolate equivalent.

In a typical procedure, the aryl halide of formula (11) is reacted with a tin enolate generated in-situ by treatment of isoprenyl acetate with tri-n-butyltin methoxide of formula $Bu_3SnOMe$ in the presence of a suitable palladium catalyst (palladium acetate/tri-ortho-tolylphosphine of formula $Pd(OAc)_2/P(o\text{-}Tol)_3$) in a non-polar solvent (e.g. toluene, benzene, hexane). Preferably, the reaction is carried out at a temperature comprised between 80° C. and 110° C. for 6 to 16 hours.

The aryl halide of formula (11) may be obtained by esterification of the corresponding acid of formula (12):

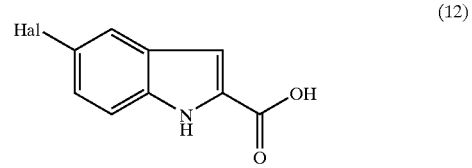

wherein Hal is as previously defined, according to any method well-known to the one skilled in the art to prepare an ester from an acid, without modifying the rest of the molecule.

In a typical procedure, the acid of formula (12) is reacted with an alcoholic solvent of formula RaOH, wherein Ra is as previously defined, in the presence of an acid such as hydrogen chloride at a temperature between 10° C. and 40° C. (room temperature) for 8 to 16 hours.

The acid of formula (12) is a commercial product.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

For some of the steps of the here above described process of preparation of the indole derivatives of formula (1), it can be necessary to protect the potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Thieme Verlag, 1994), can be used.

Also, the indole derivatives of formula (1) as well as intermediate for the preparation thereof can be purified according to various well-known methods, such as for example crystallization or chromatography.

Preferred compounds of formula (1) are those wherein n is 1 or 2;

$R_1$ is a $(C_1–C_4)$alkyl;

$R_2$ is selected from hydrogen and $(C_1–C_4)$alkyl;

$R_3$ is selected from hydrogen and $(C_1–C_6)$alkyl; and, $R_4$, $R_5$, $R_6$, $R_7$ and $R_8$ are each independently selected from the group consisting of hydrogen, hydroxy, $(C_1–C_6)$alkyl, $(C_1–C_6)$alkoxy, benzyloxy, hydroxy $(C_1–C_6)$alkyl, thio$(C_1–C_6)$alkyl, halo and trifluoromethyl, or, if appropriate, their pharmaceutically acceptable salts and/or isomers, tautomers, solvates or isotopic variations thereof.

More preferred compounds of formula (1) are those wherein n is an integer equal to 1 or 2;

$R_1$ is selected from methyl and ethyl $R_2$ is selected from hydrogen, methyl and ethyl;

$R_3$ is selected from hydrogen and methyl; and $R_4$, $R_5$, $R_6$, $R_7$ and $R_8$ are each independently selected from the group consisting of hydrogen, hydroxy, $(C_1–C_6)$alkyl, $(C_1–C_6)$alkoxy, benzyloxy, hydroxy $(C_1–C_6)$alkyl, thio$(C_1–C_6)$alkyl, halo and trifluoromethyl, or, if appropriate, their pharmaceutically acceptable salts and/or isomers, tautomers, solvates or isotopic variations thereof, Still more preferred compounds are those wherein n is an integer equal to 1 or 2;

$R_1$ is selected from methyl and ethyl;

$R_2$ is selected from hydrogen, methyl and ethyl;

$R_3$ is selected from hydrogen or methyl; and $R_4$, $R_5$, $R_6$, $R_7$ and $R_8$ are each independently selected from the group consisting of hydrogen, hydroxy, methyl, methoxy, ethoxy, benzyloxy, thiomethyl, halo and trifluoromethyl, or, if appropriate, their pharmaceutically acceptable salts and/or isomers, tautomers, solvates or isotopic variations thereof, Preferably, at least 2 of $R_4$, $R_5$, $R_6$, $R_7$ and $R_8$ are hydrogen.

Particularly preferred are the indole derivatives of the formula (1) in which n is equal to 1 or 2, $R_1$ is methyl, $R_2$ and $R_3$ are hydrogen atoms, and $R_4$, $R_5$, $R_6$, $R_7$ and $R_8$ are each independently selected from the group consisting of hydrogen, hydroxy, $(C_1$–$C_6)$alkyl, $(C_1$–$C_6)$alkoxy, hydroxy $(C_1$–$C_6)$alkyl, thio$(C_1$–$C_6)$alkyl, halo and trifluoromethyl, or, if appropriate, their pharmaceutically acceptable salts and/or isomers, tautomers, solvates or isotopic variations thereof.

More particularly preferred are the indole derivatives of the formula (1) in which n is equal to 1, $R_1$ is methyl, $R_2$ and $R_3$ are hydrogen atoms, and $R_4$, $R_5$, $R_6$, $R_7$ and $R_8$ are each independently selected from the group consisting of hydrogen, hydroxy, $(C_1$–$C_6)$alkyl, $(C_1$–$C_6)$alkoxy, thio $(C_1$–$C_6)$alkyl and trifluoromethyl or, if appropriate, their pharmaceutically acceptable salts and/or isomers, tautomers, solvates or isotopic variations thereof.

Still more particularly preferred are the indole derivatives of the formula (1) in which n is equal to 1, $R_1$ is methyl, $R_2$ and $R_3$ are hydrogen atoms, and $R_4$, $R_5$, $R_6$, $R_7$ and $R_8$ are each independently selected from the group consisting of hydrogen, $(C_1$–$C_6)$alkyl, $(C_1$–$C_6)$alkoxy and trifluoromethyl, provided that at least 2 of $R_4$, $R_5$, $R_6$, $R_7$ and $R_8$ are hydrogen, or, if appropriate, their pharmaceutically acceptable salts and/or isomers, tautomers, solvates or isotopic variations thereof.

Still more particularly preferred are the indole derivatives of the formula (1) in which n is equal to 1, $R_1$ is methyl, $R_2$ and $R_3$ are hydrogen atoms, and $R_4$, $R_5$, $R_6$, $R_7$ and $R_8$ are each independently selected from the group consisting of hydrogen, methyl, methoxy and trifluoromethyl provided that at least 2 of $R_4$, $R_5$, $R_6$, $R_7$ and $R_8$ are hydrogen, or, if appropriate, their pharmaceutically acceptable salts and/or isomers, tautomers, solvates or isotopic variations thereof.

Particularly preferred are the indole derivatives of the formula (1) as described in the Examples section hereafter, i.e.:

5-[(2R)-2-({(2R)-2-hydroxy-2-[4-hydroxy-3-(hydroxymethyl)phenyl]ethyl}amino)propyl]-N-(2-methoxybenzyl)-1H-indole-2-carboxamide, 5-[(2R)-2-({(2R)-2-hydroxy-2-[4-hydroxy-3-(hydroxymethyl)phenyl]ethyl}amino)propyl]-N-[4-(trifluoromethyl)benzyl]-1H-indole-2-carboxamide, N-(2,6-dimethoxybenzyl)-5-[(2R)-2-({(2R)-2-hydroxy-2-[4-hydroxy-3-(hydroxymethyl)phenyl]ethyl}amino) propyl]-1H-indole-2-carboxamide, 5-[(2R)-2-({(2R)-2-hydroxy-2-[4-hydroxy-3-(hydroxymethyl)phenyl]ethyl}amino)propyl]-N-(3-methoxybenzyl)-1H-indole-2-carboxamide, 5-[(2R)-2-({(2R)-2-hydroxy-2-[4-hydroxy-3-(hydroxymethyl)phenyl]ethyl}amino)propyl]-N-[2-(3-methoxyphenyl)ethyl]-1H-indole-2-carboxamide, 5-[(2R)-2-({(2R)-2-Hydroxy-2-(4-hydroxy-3-hydroxymethyl phenyl)ethyl}amino)propyl}-N-(2,4-dichlorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(3-hydroxy-2,6-dimethoxybenzyl)-1H-indole-2-carboxamide, 5-[(2R)-2-({(2R)-2-Hydroxy-2-(4-benzyloxy-3-hydroxy methyl phenyl)ethyl}amino)propyl}-N-(2-benzyloxy-6-methoxybenzyl)-1H-indole-2-carboxamide, 5-[(2R)-2-({(2R)-2-Hydroxy-2-(4-hydroxy-3-hydroxymethyl phenyl)ethyl}amino) propyl}-N-(4-hydroxy-2,6-dimethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-benzyloxy-6-methoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-hydroxy-6-methoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2,6-difluorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-chlorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-fluorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(4-hydroxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(3-hydroxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-methylsulfanylbenzyl)-1H-indole-2-carboxamide, 5-[(2R)-2-({(2R)-2-Hydroxy-2-(4-hydroxy-3-hydroxymethyl phenyl)ethyl}amino)propyl}-N-(4-methylsulfanylbenzyl)-1H-indole-2-carboxamide, 5-[(2R)-2-({(2R)-2-Hydroxy-2-(4-hydroxy-3-hydroxymethyl phenyl)ethyl}amino)propyl}-N-(2,3-dimethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2,4-dimethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-ethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-benzyl-N-methyl-1H-indole-2-carboxamide,

[(2R)-2-({(2R)-2-Hydroxy-2-(4-hydroxy-3-hydroxymethyl phenyl)ethyl}amino)propyl}-N-benzyl-1H-indole-2-carboxamide,

[(2R)-2-({(2R)-2-Hydroxy-2-(4-hydroxy-3-hydroxymethyl phenyl)ethyl}amino)propyl}-N-(4-fluorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-methoxy-3-methyl-benzyl)-1H-indole-2-carboxamide, 5-[(2R)-2-({(2R)-2-Hydroxy-2-(4-hydroxy-3-hydroxymethyl phenyl)ethyl}amino)propyl}-N-(3-methoxy-2-methylbenzyl)-1H-indole-2-carboxamide, 1-Ethyl-5-[(2R)-2-(((2R)-2-hydroxy-2-(4-hydroxy-3-hydroxy methylphenyl)ethyl}amino)propyl}-N-(2,6-dimethoxybenzyl)-1H-indole-2-carboxamide, 1-Ethyl-5-[(2R)-2-({(2R)-2-hydroxy-2-(4-hydroxy-3-hydroxy methylphenyl)ethyl}amino)propyl}-N-(2-ethoxybenzyl)-1H-indole-2-carboxamide, 1-Ethyl-5-[(2R)-2-({(2R)-2-hydroxy-2-(4-hydroxy-3-hydroxy methylphenyl)ethyl}amino)propyl}-N-(4-chlorobenzyl)-1H-indole-2-carboxamide, 1-Methyl-5-[(2R)-2-({(2R)-2-hydroxy-2-(4-hydroxy-3-hydroxy methylphenyl)ethyl}amino)propyl}-N-(2,6-dimethoxybenzyl)-1H-indole-2-carboxamide, 1-Methyl-5-[(2R)-2-({(2R)-2-hydroxy-2-(4-hydroxy-3-hydroxy methylphenyl)ethyl}amino)propyl}-N-(2-methoxybenzyl)-1H-indole-2-carboxamide, 1-Methyl-5-[(2R)-2-({(2R)-2-hydroxy-2-(4-hydroxy-3-hydroxy methylphenyl)ethyl}amino)propyl}-N-(4-chlorobenzyl)-1H-indole-2-carboxamide, 5-[(2R)-2-({(2R)-2-Hydroxy-2-(4-hydroxy-3-hydroxymethyl phenyl)ethyl}amino)butyl}-N-(2-methoxybenzyl)-1H-indole-2-carboxamide,
5-[(2R)-2-({(2R)-2-Hydroxy-2-(4-hydroxy-3-hydroxymethyl phenyl)ethyl}amino)butyl}-N-(2,6-dimethoxybenzyl)-1H-indole-2-carboxamide,
5-[(2R)-2-({(2R)-2-Hydroxy-2-(4-hydroxy-3-hydroxymethyl phenyl)ethyl}amino)butyl}-N-(2-ethoxybenzyl)-1H-indole-2-carboxamide, and,
5-[(2R)-2-({(2R)-2-Hydroxy-2-(4-hydroxy-3-hydroxymethyl phenyl)ethyl}amino)butyl}-N-benzyl-1H-indole-2-carboxamide.

The indole derivatives of formula (1) may also be optionally transformed into pharmaceutically acceptable salts. In particular, these pharmaceutically acceptable salts of the indole derivatives of the formula (1) include the acid addition and the base salts thereof.

Suitable acid addition salts are formed from mineral or organic non-toxic acids which form non-toxic salts. Suitable examples of these acid addition salts are the hydrochloride, hydrobromide, hydroiodide, hydrogen sulphate, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate, pamoate and xinafoate salts.

Suitable base salts are formed from bases, which form non-toxic salts, such as alkali metal salts, earth metal salts or addition salts with ammonia and physiologically tolerable organic amines. Suitable examples of these base salts are the sodium, potassium, aluminium, calcium, magnesium, zinc or ammonium salts as well as addition salts with triethylamine, ethanolamine, diethanolamine, trimethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, quinine, choline, arginine, lysine, leucine, dibenzylamine, tris(2-hydroxyethyl)amine, or α,α,α-tris(hydroxymethyl)methylamine.

Compounds which contain both acidic groups and basic groups can also be present in the form of internal salts or betaines, which are also included by the present invention. For a review on suitable salts see Berge et al., *J. Pharm. Sci.*, 1977, 66, p. 1–19.

Salts can generally be obtained from the indole derivatives of the formula (1) according to customary procedures known to the person skilled in the art, for example by combining with an organic or inorganic acid or base solvent or dispersant, or alternatively from other salts by anion exchange or cation exchange. The salt may precipitate from solution and be collected by filtration or may be recovered by evaporation of the solvent.

The indole derivatives of the formula (1) can also be present in stereoisomeric forms. If the indole derivatives of the formula (1) contain one or more centres of asymmetry, these can independently of one another have the (S) configuration or the (R) configuration. The invention includes all possible stereoisomers of the indole derivatives of the formula (1), for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. The invention likewise relates to diastereomers in diastereomerically pure form and in the form of mixtures in all ratios. In the presence of cis/trans isomerism, the invention relates to both the cis form and the trans form and mixtures of these forms in all ratios. Individual stereoisomers can be prepared, if desired, by use of stereochemically homogeneous starting substances in the synthesis, by stereoselective synthesis or by separation of a mixture according to customary methods, for example by chromatography, crystallization or by chromatography on chiral phases. If appropriate, derivatization can be carried out before separation of stereoisomers. A stereoisomer mixture can be separated at the stage of the indole derivatives of the formula (1) or at the stage of a starting substance or of an intermediate in the course of the synthesis.

According to one aspect of the present invention, the following R-stereoisomer wherein $R_1$ to $R_8$ and n are as defined above, is generally preferred,

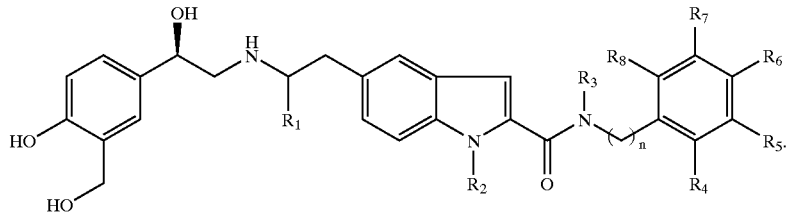

When $R_1$ is $(C_1–C_4)$alkyl, the following (R,R)-stereoisomer $R_1$ to $R_8$ and n are as defined above, is generally preferred,

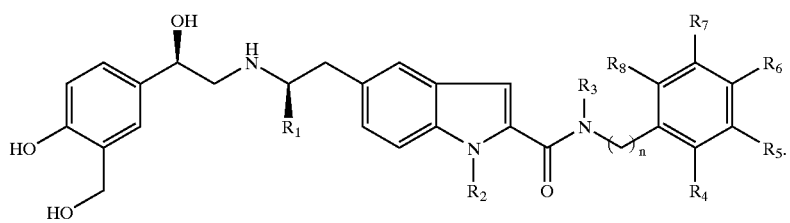

The compounds of the formula (1) according to the invention can moreover contain mobile hydrogen atoms, i.e. be present in various tautomeric forms. The present invention also relates to all tautomers of the compounds of the formula (1).

The present invention furthermore includes other types of derivatives of indole derivatives of the formula (1), for example, solvates such as hydrates and polymorphs, i.e. the various different crystalline structures of the indole derivatives according to the present invention.

The present invention also includes all suitable isotopic variations of the indole derivatives of the formula (1) or a pharmaceutically acceptable salt thereof. An isotopic variation of the indole derivatives of the formula (1) or a pharmaceutically acceptable salt thereof is defined as one in which at least one atom is replaced by an atom having the same atomic number but an atomic mass different from the atomic mass usually found in nature. Examples of isotopes that can be incorporated into the indole derivatives of the formula (1) and pharmaceutically acceptable salts thereof include isotopes of hydrogen, carbon, nitrogen, oxygen, sulphur, fluorine and chlorine such as $^{2}H$, $^{3}H$, $^{13}C$, $^{14}C$, $^{15}N$, $^{17}O$, $^{18}O$, $^{35}S$, $^{18}F$ and $^{36}Cl$, respectively. Certain isotopic variations of the indole derivatives of the formula (1) and pharmaceutically acceptable salts thereof, for example, those in which a radioactive isotope such as $^{3}H$ or $^{14}C$ is incorporated, are useful in drug and/or substrate tissue distribution studies. Tritiated, i.e. $^{3}H$, and carbon-14, i.e. $^{14}C$, isotopes are particularly preferred for their ease of preparation and detectability. Further, substitution with isotopes such as deuterium, i.e. $^{2}H$, may afford certain therapeutic advantages resulting from greater metabolic stability, for example, increased in vivo half-life or reduced dosage requirements and hence may be preferred in some circumstances. Isotopic variations of the indole derivatives of the formula (1) and pharmaceutically acceptable salts thereof of this invention can generally be prepared by conventional procedures such as by the illustrative methods or by the preparations described in the Examples and Preparations sections hereafter using appropriate isotopic variations of suitable reagents.

According to a further aspect, the present invention concerns mixtures of indole derivatives of the formula (1), as well as mixtures with or of their pharmaceutically acceptable salts, solvates, isomeric forms and/or isotope forms.

According to the present invention, all the here above mentioned forms of the indole derivatives of formula (1) except the pharmaceutically acceptable salts (i.e. said solvates, isomeric forms, tautomers and isotope forms), are defined as "derived forms" of the indole derivatives of formula (1) in what follows (including the claims).

The indole derivatives of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases.

The indole derivatives of formula (1) and their pharmaceutically acceptable salts and derived forms as mentioned above can be administered according to the invention to animals, preferably to mammals, and in particular to humans, as pharmaceuticals for therapy and/or prophylaxis. They can be administered per se, in mixtures with one another or in the form of pharmaceutical preparations which as active constituent contain an efficacious dose of at least one indole derivative of the formula (1), its pharmaceutically acceptable salts and/or derived forms, in addition to customary pharmaceutically innocuous excipients and/or additives.

Thus, the present invention also relates to compositions containing an indole derivative of formula (1) and/or their pharmaceutically acceptable salts and/or derived forms, together with customary pharmaceutically innocuous excipients and/or additives. Such compositions are prepared according to well-known methods compatible with the standard pharmaceutical practice. Said compositions generally contain from 0.5% to 60% in weight of the active compound and from 40% to 99.5% in weight of excipients and/or additives. According to the present invention, said excipients and/or additives are agents well known to the artisan for providing favourable properties in the final pharmaceutical composition. Typical excipients and/or additives include, but are by no means limited to, acidifying and alkalizing agents, aerosol propellants, anti-microbial agents (including anti-bacterial, anti-fungal and anti-protozoal agents), antioxidants, buffering agents, chelating agents, dispersing agents, suspending agents, emollients, emulsifying agents, preservatives, sequestering agents, solvents, stabilizers, stiffening agents, sugars, surfactants and flavouring agents. Furthermore, said compositions are prepared in a form compatible for the intended route of administration, which is used for any given patient, as well as appropriate to the disease, disorder or condition for which any given patient is being treated. Suitable routes of administration that can be envisaged are for example the topical, oral, inhaled, rectal, intra-veinous, intra-arterial, intra-peritoneal, intra-thecal, intra-ventricular, intra-urethral, intra-sternal, intra-cranial, intra-muscular, subcutaneous or ocular routes. In the present case, the inhalation route is preferred.

When an administration by the oral route is intended, the indole derivatives of formula (1), their pharmaceutically acceptable salts and/or their derived forms, can be administered in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The indole derivatives of formula (1), their pharmaceutically acceptable salts and/or their derived forms, may also be administered as fast-dispersing or fast-dissolving dosage forms or in the form of a high energy dispersion or as coated particles. Suitable formulations of the indole derivatives of formula (1), their pharmaceutically acceptable salts and/or their derived forms, may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

As a general example, a formulation of the tablet could typically contain between about 0.001 mg and 5000 mg of active compound whilst tablet fill weights may range from 50 mg to 5000 mg. The tablets may be manufactured by a standard process, for example by direct compression or by a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the indole derivatives of the formula (1), their pharmaceutically acceptable salts and/or their derived forms, may be combined with various sweetening or flavouring agents, colouring matter or dyes, with emulsifying and/or suspending agents and with diluents such as water, ethanol, propylene glycol and glycerin, and combinations thereof.

The indole derivatives of the formula (1), their pharmaceutically acceptable salts and/or their derived forms, can also be administered by injection, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of such formulations under sterile conditions is readily accomplished by standard pharmaceutical techniques well-known to those skilled in the art.

For both oral administration and injection to human patients, the daily dosage level of the indole derivatives of the formula (1), their pharmaceutically acceptable salts and/or their derived forms, will usually be from 0.001 mg/kg to 1000 mg/kg (in single or divided doses).

The indole derivatives of the formula (1), their pharmaceutically acceptable salts and/or their derived forms, can also be administered by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an indole derivative of the formula (1) and a suitable powder base such as lactose or starch.

Aerosol or dry powder formulations are preferably arranged so that each metered dose or "puff" contains from 0.001 mg to 10 mg of an indole derivative of the formula (1) for delivery to the patient. The overall daily dose with an aerosol will be in the range of from 0.001 mg to 40 mg, which may be administered in a single dose or, more usually, in divided doses throughout the day.

The indole derivatives of the formula (1), their pharmaceutically acceptable salts and/or their derived forms, can also be administered topically, or transdermally, in the form of creams, gels, suspensions, lotions, ointments, dusting powders, sprays, foams, mousses, drug-incorporated dressings, solutions, sponges, fibres, microemulsions, films, skin patches, ointments such as petrolatum or white soft paraffin based ointments or via a skin patch or other device. Penetration enhancers may be used, and the compound may be used in combination with cyclodextrins. In addition, the compound may be delivered using iontophoresis, electropration, phonophoresis or sonophoresis. They could be administered directly onto a wound site. They could be incorporated into a coated suture. For example they can be incorporated into a lotion or cream consisting of an aqueous or oily emulsion of mineral oils, sorbitan monostearate, polysorbate 60, cetyl esters wax, cetearyl alcohol, 2-octyldodecanol, benzyl alcohol, water, polyethylene glycols and/or liquid paraffin, or they can be incorporated into a suitable ointment consisting of one or more of the following: mineral oil, liquid petrolatum, white petrolatum, propylene glycol, polyoxyethylene polyoxypropylene compound, emulsifying wax and water, or as hydrogel with cellulose or polyacrylate derivatives or other viscosity modifiers, or as a dry powder or liquid spray or aerosol with butane/propane, HFA, CFC, $CO_2$ or other suitable propellant, optionally also including a lubricant such as sorbitan trioleate, or as a drug-incorporated dressing either as a tulle dressing, with white soft paraffin or polyethylene glycols impregnated gauze dressings or with hydrogel, hydrocolloid, alginate or film dressings.

For topical administration to human patients with acute/surgical wounds or scars, the daily dosage level of the compounds, in suspension or other formulation, could be from 0.001 to 50 mg/ml, preferably from 0.03 to 30 mg/ml. The dosage will vary with the size of the wound, whether or not the wound is open or closed or partially closed, and whether or not the skin is intact.

Alternatively, the indole derivatives of the formula (1), their pharmaceutically acceptable salts and/or their derived forms, can be rectally administered, for example in the form of a suppository of a gel, although other forms can be considered.

They may also be administered by the ocular route, in particular for ocular scarring. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The various pharmaceutical formulations as decribed here above are also detailed in "Pharmacie galénique" from A. Lehir (Ed. Mason, 1992, $2^{nd}$ edition).

The physician in any event will determine the actual dosage which will be most suitable for any individual patient and it will vary with the age, weight, health state and sex of the patient as well as the severity of the disease, disorder or condition to treat, the optional combination with other treatment(s), the response of the particular patient and in general any factor peculiar to the concerned disease, disorder or condition and to the patient. Thus, the daily dose in human may usually contain from 0.001 mg to 5000 mg of active compound for administration singly or two or more at a time, as appropriate. There can, of course, be individual instances where higher or lower dosage ranges are merited and such are within the scope of this invention.

According to the present invention, the indole derivatives of the formula (1), their pharmaceutically acceptable salts and/or their derived forms, may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. α-, β- and γ-cyclodextrins are most commonly used and suitable examples are described in WO-A-91/11172, WO-A-94/02518 and WO-A-98/55148.

According to another embodiment of the present invention, the indole derivatives of the formula (1), or pharmaceutically acceptable salts, derived forms or compositions thereof, can also be used as a combination with one or more additional therapeutic agents to be co-administered to a patient to obtain some particularly desired therapeutic end result. The second and more additional therapeutic agents may also be an indole derivative of the formula (1), or pharmaceutically acceptable salts, derived forms or compositions thereof, or one or more β2 agonists known in the art. More typically, the second and more therapeutic agents will be selected from a different class of therapeutic agents.

As used herein, the terms "co-administration", "co-administered" and "in combination with", referring to the indole derivatives of formula (1) and one or more other therapeutic agents, is intended to mean, and does refer to and include the following simultaneous administration of such combination of indole derivative(s) and therapeutic agent(s) to a patient in need of treatment, when such components are formulated together into a single dosage form which releases said components at substantially the same time to said patient, substantially simultaneous administration of such combination of indole derivative(s) and therapeutic agent(s) to a patient in need of treatment, when such components are formulated apart from each other into separate dosage forms which are taken at substantially the same time by said patient, whereupon said components are released at substantially the same time to said patient, sequential administration of such combination of indole derivative(s) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of indole derivative(s) and therapeutic agent(s) to a patient in need of treatment, when such components are formulated together into a single dosage form which releases said components in a controlled manner whereupon they are concurrently, consecutively, and/or overlappingly administered at the same and/or different times by said patient, where each part may be administered by either the same or different route.

Suitable examples of other therapeutic agents which may be used in combination with the indole derivatives of the formula (1), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids,
(k) Monoclonal antibodies active against endogenous inflammatory entities,
(l) Anti-tumor necrosis factor (anti-TNF-α) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFκβ pathway, e.g. IKK inhibitors,
(w) Agents that can be classed as mucolytics or anti-tussive, and
(x) Antibiotics.

According to the present invention, combination of the indole derivatives of formula (1) with:

glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, and mometasone furoate, or muscarinic M3 receptor antagonists or anticholinergic agents including in particular ipratropium salts, namely bromide, tiotropium salts, namely bromide, oxitropium salts, namely bromide, perenzepine, and telenzepine, are preferred.

It is to be appreciated that all references herein to treatment include curative, palliative and prophylactic treatment. The description, which follows, concerns the therapeutic applications to which the indole derivatives of formula (1) may be put.

The indole derivatives of formula (1) have the ability to interact with the β2 receptor and thereby have a wide range of therapeutic applications, as described further below, because of the essential role which the β2 receptor plays in the physiology of all mammals.

Therefore, a further aspect of the present invention relates to the indole derivatives of formula (1), or pharmaceutically acceptable salts, derived forms or compositions thereof, for use in the treatment of diseases, disorders, and conditions in which the β2 receptor is involved. More specifically, the present invention also concerns the indole derivatives of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis, premature labor, and other type of diseases and conditions such as inflammatory and allergic skin diseases, psoriasis and proliferative skin diseases.

A still further aspect of the present invention also relates to the use of the indole derivatives of formula (1), or pharmaceutically acceptable salts, derived forms or compositions thereof, for the manufacture of a drug having a β2 agonist activity. In particular, the present inventions concerns the use of the indole derivatives of formula (1), or pharmaceutically acceptable salts, derived forms or compositions thereof, for the manufacture of a drug for the treatment of β2-mediated diseases and/or conditions, in particular the diseases and/or conditions listed above.

As a consequence, the present invention provides a particularly interesting method of treatment of a mammal, including a human being, including treating said mammal with an effective amount of an indole derivative of formula (1), or a pharmaceutically acceptable salt, derived form or composition thereof. More precisely, the present invention provides a particularly interesting method of treatment of a mammal, including a human being, to treat a β2-mediated diseases and/or conditions, in particular the diseases and/or conditions listed above, including treating said mammal with an effective amount of an indole derivative of formula (1), its pharmaceutically acceptable salts and/or derived forms.

The following examples illustrate the preparation of the indole derivatives of the formula (1):

EXAMPLE 1

5-[(2R)-2-({(2R)-2-hydroxy-2-[4-hydroxy-3-(hydroxymethyl)phenyl]ethyl}amino)propyl]-N-(2-methoxybenzyl)-1H-indole-2-carboxamide

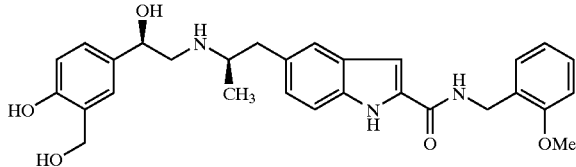

A solution of 5-[(2R)-2-({(2R)-2-{[tert-butyl(dimethyl)silyl]oxy}-2-[4-hydroxy-3-(hydroxymethyl)phenyl]ethyl}amino)propyl]-N-(2-methoxybenzyl)-1H-indole-2-carboxamide (Preparation 1, 67 mg, 0.11 mmol) in a mixture of methanol (4.0 ml) and water (2.4 ml) was treated with ammonium fluoride (40 mg, 1.08 mmol) and the resulting suspension heated at 40° C. for a period of 16 hours. The solvent was removed in vacuo and the residue purified by flash column chromatography on silica gel eluting with dichloromethane:methanol 0.88 ammonia (95:5:0.5 changing to 85:15:1.5, by volume) to give the title compound as a colourless solid (38 mg).

$^1$H NMR (400 MHz, CD$_3$OD): δ=7.35–7.19 (5H, m), 7.03–6.96 (4H, m), 6.93–6.89 (1H, m), 6.63–6.61 (1H, d), 4.65–4.62 (1H, m), 4.59 (2H, s), 4.57 (2H, s), 3.88 (3H, s), 3.09–3.04 (1H, m), 2.98–2.93 (1H, m), 2.85–2.69 (3H, m), 1.14–1.12 (3H, d) ppm.

LRMS (electrospray): m/z [M+H]$^+$ 504.

Analysis: Found C, 65.86; H, 6.57; N, 7.71; C$_{29}$H$_{33}$N$_3$O$_5$·1.4H$_2$O requires C, 65.87; H, 6.82; N, 7.95.

Optical Rotation [α]$^D_{25}$=−351.07° 0.4 mg/ml MeOH, 365 nm

EXAMPLE 2

5-[(2R)-2-({(2R)-2-hydroxy-2-[4-hydroxy-3-(hydroxymethyl)phenyl]ethyl}amino)propyl]-N-[4-(trifluoromethyl)benzyl]-1H-indole-2-carboxamide

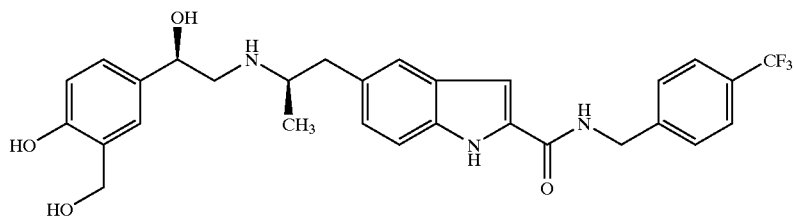

Prepared from 5-[(2R)-2-({(2R)-2-{[tert-butyl(dimethyl)silyl]oxy}-2-[4-hydroxy-3-(hydroxymethyl)phenyl]ethyl}amino)propyl]-N-[4-(trifluoromethyl)benzyl]-1H-indole-2-carboxamide (Preparation 2) according to the method described above to give the title compound as a pale yellow foam.

$^1$H NMR (400 MHz, CD$_3$OD): δ=7.65–7.63 (2H, m), 7.57–7.55 (2H, m), 7.34–7.32 (2H, m), 7.17 (1H, s), 7.03–6.94 (3H, m), 6.60–6.58 (1H, d), 4.67 (2H, s), 4.61–4.58 (1H, m), 4.55 (2H, s), 3.00–2.89 (2H, m), 2.78–2.67 (3H, m), 1.12–1.10 (3H, d) ppm.

LRMS (electrospray): m/z [M+H]$^+$ 542.

EXAMPLE 3

N-(2,6-dimethoxybenzyl)-5-[(2R)-2-({(2R)-2-hydroxy-2-[4-hydroxy-3-(hydroxymethyl)phenyl]ethyl}amino)propyl]-1H-indole-2-carboxamide Prepared from 5-[(2R)-2-({(2R)-2-{[tert-butyl(dimethyl)silyl]oxy}-2-[4-hydroxy-3-(hydroxymethyl)phenyl]ethyl}amino)propyl]-N-(3-methoxybenzyl)-1H-indole-2-carboxamide (Preparation 4) according to the method described above to give the title compound as a colourless foam.

$^1$H NMR (400 MHz, CD$_3$OD): δ=7.34–4.31 (2H, d), 7.26–7.21 (1H, t), 7.18–7.17 (1H, m), 7.05–6.94 (5H, m), 6.82–6.80 (1H, m), 6.61–6.59 (1H, d), 4.62–4.56 (5H, m), 3.77 (3H, s), 3.02–2.89 (2H, m), 2.76–2.69 (3H, m), 1.12–1.10 (3H, d) ppm.

LRMS (electrospray): m/z [M+H]$^+$ 504.

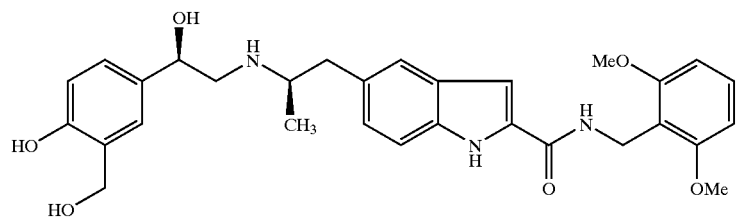

Prepared from 5-[(2R)-2-({(2R)-2-{[tert-butyl(dimethyl)silyl]oxy}-2-[4-hydroxy-3-(hydroxymethyl)phenyl]ethyl}amino)propyl]-N-(2,6-dimethoxybenzyl)-1H-indole-2-carboxamide (Preparation 3) according to the method described above to give the title compound as a colourless solid.

$^1$H NMR (400 MHz, CD$_3$OD): δ=7.29–7.24 (3H, m), 7.16 (1H, bs), 6.97–6.92 (3H, m), 6.66 (2H, d), 6.58 (1H, d), 4.66 (2H, s), 4.59–4.55 (1H, m), 4.54 (2H, s), 3.66 (6H, s), 2.94–2.86 (2H, m), 2.70–2.64 (3H, m), 1.08 (3H, d) ppm.

LRMS (electrospray): m/z [M+H]$^+$ 534, [M+Na]$^+$ 556.

Analysis: Found C, 66.42; H, 6.69; N, 7.88; C$_{29}$H$_{33}$N$_3$O$_5$·0.52H$_2$O requires C, 66.36; H, 6.69; N, 7.74.

EXAMPLE 4

5-[(2R)-2-({(2R)-2-hydroxy-2-[4-hydroxy-3-(hydroxymethyl)phenyl]ethyl}amino)propyl]-N-(3-methoxybenzyl)-1H-indole-2-carboxamide

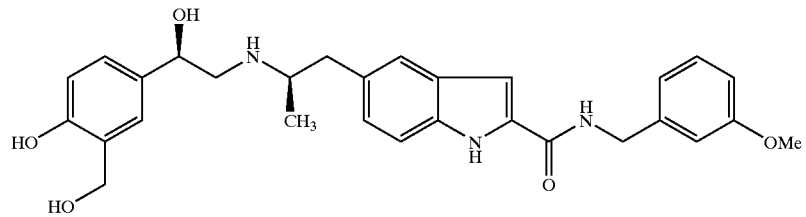

EXAMPLE 5

5-[(2R)-2-({(2R)-2-hydroxy-2-[4-hydroxy-3-(hydroxymethyl)phenyl]ethyl}amino)propyl]-N-[2-(3-methoxyphenyl)ethyl]-1H-indole-2-carboxamide

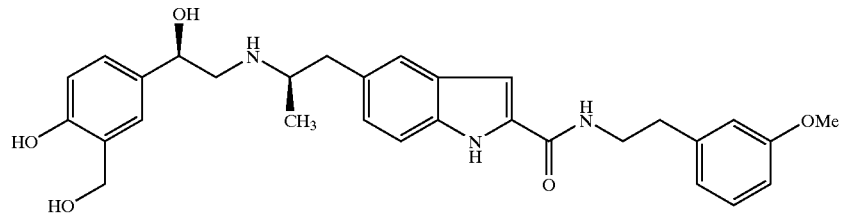

Prepared from 5-[(2R)-2-({(2R)-2-{[tert-butyl(dimethyl)silyl]oxy}-2-[4-hydroxy-3-(hydroxymethyl)phenyl]ethyl}amino)propyl]-N-[2-(3-methoxyphenyl)ethyl]-1H-indole-2-carboxamide (Preparation 5) according to the method described above to give the title compound as a colourless foam.

$^1$H NMR (400 MHz, CD$_3$OD): δ=7.33–7.31 (2H, d), 7.21–7.17 (2H, m), 7.01–6.93 (3H, m), 6.85–6.84 (2H, m), 6.77–6.74 (1H, m), 6.61–6.59 (1H, d), 4.63–4.60 (1H, m), 4.56 (2H, s), 3.74 (3H, s), 3.62–3.58 (2H, t), 3.03–2.98 (1H, m), 2.94–2.88 (3H, m), 2.81–2.67 (3H, m), 1.12–1.10 (3H, d) ppm.

LRMS (electrospray): m/z [M+H]$^+$ 518.

EXAMPLE 6

5-[(2R)-2-({(2R)-2-Hydroxy-2-(4-hydroxy-3-hydroxymethyl phenyl)ethyl}amino)propyl}-N-(2,4-dichlorobenzyl)-1H-indole-2-carboxamide

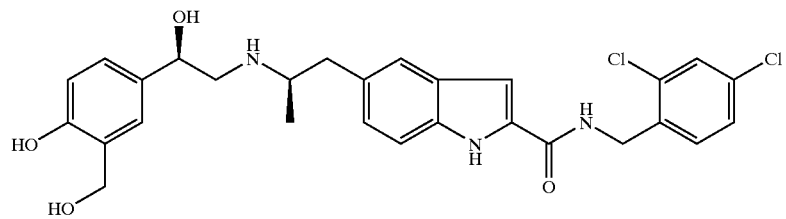

Prepared using the amide from Preparation 6 and the method described for Example 1.

$^1$H NMR (400 MHz, CD$_3$OD): δ=7.48–7.47 (1H, d), 7.44–7.42 (1H, d), 7.34–7.30 (3H, m), 7.17 (1H, s), 7.05 (1H, s), 7.03–6.95 (2H, m), 6.61–6.59 (1H, d), 4.65 (2H, s), 4.63–4.59 (1H, m), 4.55 (2H, s), 3.03–2.98 (1H, m), 2.96–2.91 (1H, m), 2.80–2.68 (3H, m), 1.13–1.11 (3H, d) ppm.

LRMS (APCI): m/z [MH]$^+$ 542.

EXAMPLE 7

5-[(2R)-2-({(2R)-2-Hydroxy-2-(4-hydroxy-3-hydroxymethyl phenyl)ethyl}amino)propyl]-N-(3-hydroxy-2,6-dimethoxybenzyl)-1H-indole-2-carboxamide

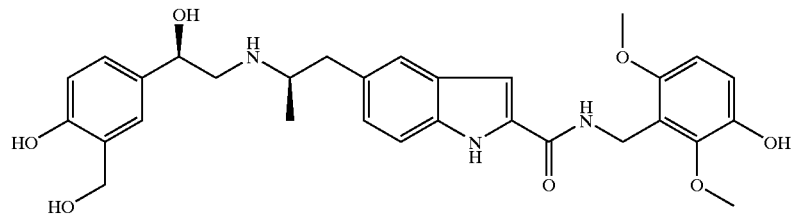

Prepared using the amide from Preparation 8 and the method described for Example 1.

$^1$H NMR (400 MHz, CD$_3$OD): δ=7.30 (2H, m), 7.17 (1H, bd), 6.96 (2H, m), 6.80 (1H, d), 6.64 (1H, d), 6.60 (1H, d), 4.65 (3H, s), 4.60 (1H, m), 4.55 (2H, s), 3.85

LRMS (ESI): m/z [M+Na]$^+$ 572.

EXAMPLE 8

5-[(2R)-2-({(2R)-2-Hydroxy-2-(4-benzyloxy-3-hydroxy methyl phenyl)ethyl}amino)propyl]-N-(2-benzyloxy-6-methoxybenzyl)-1H-indole-2-carboxamide

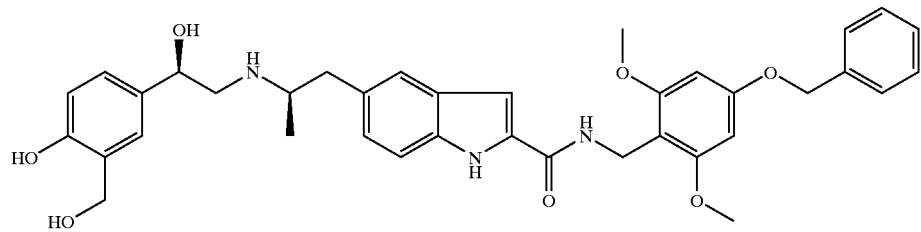

Prepared using the amide from Preparation 9 and the method described for Example 1.

$^1$H NMR (400 MHz, CD$_3$OD): δ=7.45 (2H, m), 7.37 (2H, m), 7.30 (3H, m), 7.16 (1H, d), 6.95 (3H, m), 6.58 (1H, d), 6.32 (2H, s), 5.12 (2H, s), 4.58 (1H, m), 4.56

LRMS (ESI): m/z [M+H]$^+$ 640, [M+Na]$^+$ 662.

EXAMPLE 9

5-[(2R)-2-({(2R)-2-Hydroxy-2-(4-hydroxy-3-hydroxymethyl phenyl)ethyl}amino)propyl]-N-(4-hydroxy-2,6-dimethoxybenzyl)-1H-indole-2-carboxamide

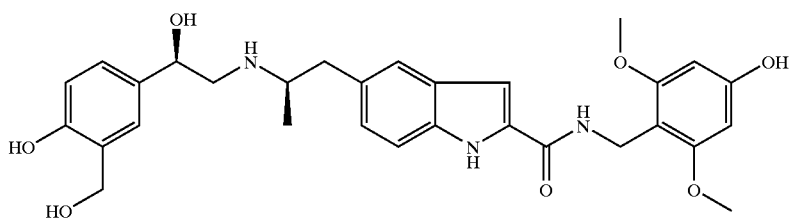

Example 8 (137 mg, 182 μmol) was hydrogenated at 50 psi at 30° C. for 6 h in ethanol (20 ml) in the presence of 10% palladium-on-carbon catalyst (20 mg). The mixture was filtered through a filter-aid and the solvent removed. The crude material was purified by chromatography (0–7% MeOH in $CH_2Cl_2$ and 1% $NH_3$) to yield a clear glass (73 mg).

$^1$H NMR (400 MHz, $CD_3OD$): δ=7.37 (1H, s), 7.34 (1H, d), 7.24 (1H, bd), 7.03 (2H, bd), 6.96 (1H, s), 6.67 (1H, d), 6.13 (2H, s), 4.71 (1H, m), 4.59 (2H, s), 4.54 (2H, s), 3.80 (6H, s), 3.22 (1H, m), 2.96 (3H, m), 2.75 (1H, m), 1.16 (3H, d) ppm.

LRMS (ESI): m/z $[M+H]^+$ 550, $[M+Na]^+$ 572.

EXAMPLE 10

5-[(2R)-2-({(2R)-2-Hydroxy-2-(4-hydroxy-3-hydroxymethyl phenyl)ethyl}amino)propyl}-N-(2-benzyloxy-6-methoxybenzyl)-1H-indol-2-carboxamide

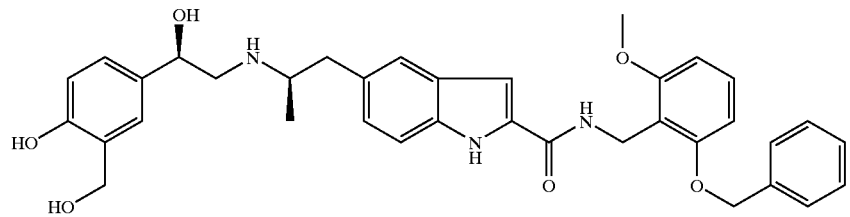

Prepared using the amide from Preparation 10 and the method described for Example 1.

$^1$H NMR (400 MHz, $CD_3OD$): δ=7.74 (1H, bd), 7.36 (6H, m), 7.15 (1H, bd), 6.96 (3H, m), 6.86 (1H, d), 6.73 (1H, d), 6.68 (1H, d), 6.58 (1H, d), 5.16 (2H, s), 4.72 (2H, s), 4.59 (1H, m), 4.54 (2H, s), 3.87 (3H, s), 3.87 (3H, s), 2.893 (2H, m), 2.70 (3H, m), 1.09 (3H, d) ppm.

LRMS (ESI): m/z $[M+H]^+$ 610, $[M+Na]^+$ 632.

EXAMPLE 11

5-[(2R)-2-({(2R)-2-Hydroxy-2-(4-hydroxy-3-hydroxymethyl phenyl)ethyl}amino)propyl}-N-(2-hydroxy-6-methoxybenzyl)-1H-indole-2-carboxamide

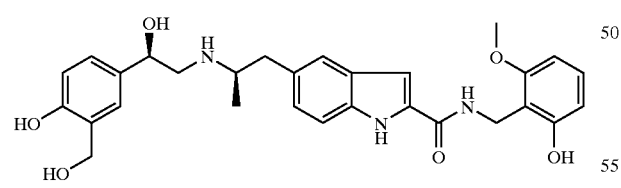

Prepared using the ether from Example 10 and the method described for Example 9.

$^1$H NMR (400 MHz, $DMSO_{d6}$): δ=11.45 (1H, s), 9.99 (1H, bs), 9.14 (1H, bs), 8.62 (1H, bs), 7.31 (1H, s), 7.28 (1H, d), 7.22 (1H, d), 7.12 (1H, s), 7.08 (1H, t), 6.96 (2H, dt), 6.65 (1H, d), 6.36 (2H, t), 4.94 (2H, m), 4.42 (5H, m), 3.77(3H, s), 2.82–2.73 (2H, m), 2.60 (1H, d), 2.43 (1H, m), 0.89 (3H, d) ppm.

LRMS (ESI): m/z $[M+H]^+$ 520, $[M+Na]^+$ 542.

EXAMPLE 12

5-[(2R)-2-({(2R)-2-Hydroxy-2-(4-hydroxy-3-hydroxymethyl phenyl)ethyl}amino)propyl}-N-(2,6-difluorobenzyl)-1H-indole-2-carboxamide

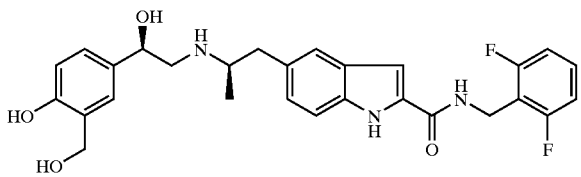

The acid from Preparation 11 (145 m g, 292 μmol) in DMF (1 ml) was treated with 2,6-difluorobenzylamine (43 mg, 301 μmol), pyridine (26 mg, 325 μmol), HOBt (43 mg, 320 μmol) in DMF (1 ml) and WSCDI (62 mg, 322 μmol) in DMF (1 ml) and the mixture shaken overnight. The solvent was removed in vacuo and replaced with DCM (2 ml) and water (0.5 ml). The organic phase was separated using a PTFE frit cartridge and the solvent removed in vacuo. Ammonium fluoride (108 mg, 292 μmol) in MeOH (1.9 ml) and water (1.1 ml) was added to the crude material and the mixture shaken at 40° C. overnight. The solvent was removed in vacuo and the crude material taken up in DMSO (1 ml) and filtered before being purified by reverse phase HPLC.

$^1$H NMR (400 MHz, $CD_3OD$): δ=7.49 (1H, s), 7.44–7.42 (1H, d), 7.39–7.32 (2H, m), 7.15–7.11 (2H, m), 7.06 (1H, s), 7.02–6.94 (2H, m), 6.78–6.76 (1H, d), 4.87 (1H, partially obscured by solvent), 4.68 (2H, s), 4.65 (2H, s), 3.61–3.54 (1H, m), 3.26–3.12 (3H, m), 2.87–2.81 (1H, m), 1.26–1.25 (3H, d) ppm.

HRMS (ESI): m/z $[M+H]^+$ found 510.2178; requires 510.2199.

EXAMPLE 13

5-[(2R)-2-({(2R)-2-Hydroxy-2-(4-hydroxy-3-hydroxymethyl phenyl)ethyl}amino)propyl}-N-(2-chlorobenzyl)-1H-indole-2-carboxamide

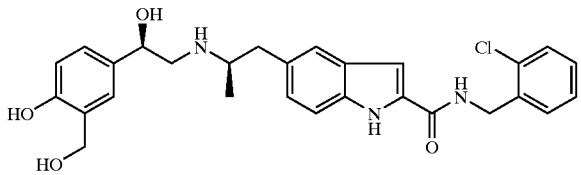

Prepared using the acid from Preparation 11 and the method described for Example 12.

$^1$H NMR (400 MHz, CD$_3$OD): δ=7.52 (1H, s), 7.46–7.40 (3H, m), 7.34 (1H, s), 7.29–7.26 (2H, m), 7.15–7.13 (3H, m), 6.78–6.76 (1H, d), 4.89 (1H, partially obscured by solvent), 4.69 (2H, s), 4.65 (2H, s), 3.63–3.55 (1H, m), 3.28–3.113 (3H, m), 2.89–2.83 (1H, m), 1.28–1.26 (3H, d) ppm.

HRMS (ESI): m/z [M+H]$^+$ found 508.1979; requires 508.1998.

EXAMPLE 14

5-[(2R)-2-({(2R)-2-Hydroxy-2-(4-hydroxy-3-hydroxymethyl phenyl)ethyl}amino)propyl}-N-(2-fluorobenzyl)-1H-indole-2-carboxamide

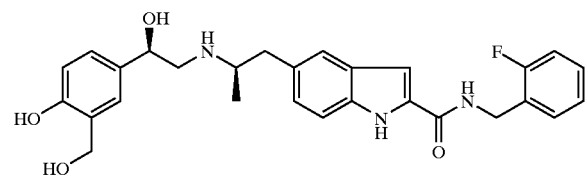

Prepared using the acid from Preparation 11 and the method described for Example 12.

$^1$H NMR (400 MHz, CD$_3$OD): δ=7.51 (1H, s), 7.45–7.40 (2H, m), 7.37–7.26 (2H, m), 7.16–7.07 (5H, m), 6.78–6.76 (1H, d), 4.88 (1H, partially obscured by solvent), 4.66–4.64 (4H, m), 3.63–3.54 (1H, m), 3.27–3.13 (3H, m), 288–2.82 (1H, m), 1.27–1.26 (3H, d) ppm.

HRMS (ESI): m/z [M+H]$^+$ found 492.2274; requires 492.2293.

EXAMPLE 15

5-[(2R)-2-({(2R)-2-Hydroxy-2-(4-hydroxy-3-hydroxymethyl phenyl)ethyl}amino)propyl}-N-(4-hydroxybenzyl)-1H-indole-2-carboxamide

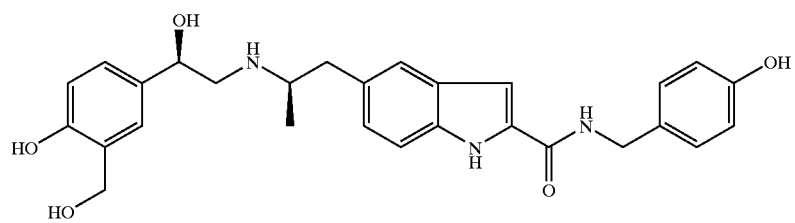

Prepared using the acid from Preparation 11 and the method described for Example 12.

$^1$H NMR (400 MHz, CD$_3$OD): δ=7.50 (1H, s), 7.44 (1H, d), 7.34 (1H, s), 7.19 (2H, d), 7.15–7.11 (2H, m), 7.06 (1H, s), 6.78–6.73 (3H, m), 4.88 (1H, partially obscured by solvent), 4.65 (2H, s), 4.48 (2H, s), 3.61–3.53 (1H, m), 3.27–3.13 (3H, m), 2.88–2.82 (1H, m), 1.27–1.26 (3H, d) ppm.

HRMS (ESI): m/z [M+H]$^+$ found 490.2321; requires 490.2337.

EXAMPLE 16

5-[(2R)-2-({(2R)-2-Hydroxy-2-(4-hydroxy-3-hydroxymethyl phenyl)ethyl}amino)propyl}-N-(3-hydroxybenzyl)-1H-indole-2-carboxamide

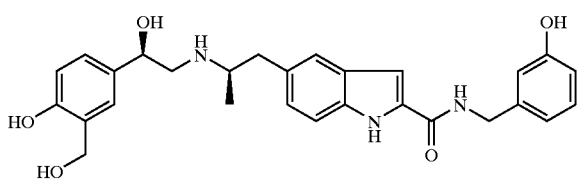

Prepared using the acid from Preparation 11 and the method described for Example 12.

$^1$H NMR (400 MHz, CD$_3$OD): δ=7.51 (1H, s), 7.46–7.43 (1H, d), 7.34 (1H, s), 7.16–7.03 (4H, m), 6.83–6.76 (3H, m), 6.68–6.66 (1H, d), 4.90 (1H, partially obscured by solvent), 4.65 (2H, s), 4.53 (2H, s), 3.63–3.54 (1H, m), 3.27–3.13 (3H, m), 2.88–2.82 (1H, m), 1.27–1.26 (3H, d) ppm.

HRMS (ESI): m/z [M+H]$^+$ found 490.2319; requires 490.2337.

EXAMPLE 17

5-[(2R)-2-({(2R)-2-Hydroxy-2-(4-hydroxy-3-hydroxymethyl phenyl)ethyl}amino)propyl}-N-(2-methylsulfanyl benzyl)-1H-indole-2-carboxamide

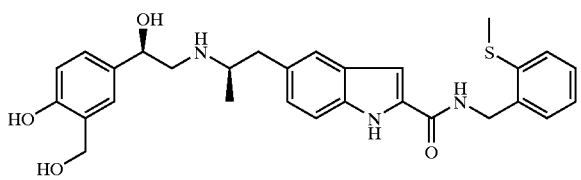

Prepared using the acid from Preparation 11 and the method described for Example 12, using 2 equivalents of pyridine.

$^1$H NMR (400 MHz, CD$_3$OD): δ=7.52 (1H, s), 7.45–7.43 (1H, d), 7.35–7.26 (4H, m), 7.17–7.11 (4H, m), 6.77 (1H, d), 4.88 (1H, partially obscured by solvent), 4.66–4.65 (4H, m), 3.63–3.55 (1H, m), 3.27–3.13 (3H, m), 2.88–2.83 (1H, m), 2.50 (3H, s), 1.27 (3H, d) ppm.

HRMS (ESI): m/z [M+H]$^+$ found 520.2246; requires 520.2265.

EXAMPLE 18

5-[(2R)-2-({(2R)-2-Hydroxy-2-(4-hydroxy-3-hydroxymethyl phenyl)ethyl}amino)propyl}-N-(4-methylsulfanylbenzyl)-1H-indole-2-carboxamide

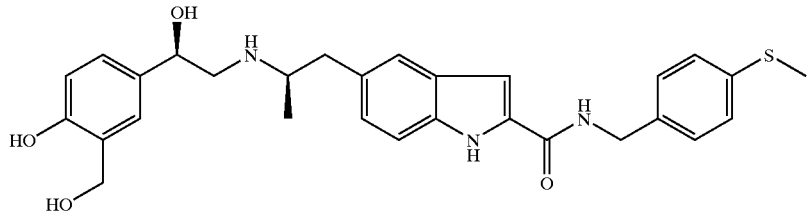

Prepared using the acid from Preparation 11 and the method described for Example 12.

$^1$H NMR (400 MHz, CD$_3$OD): δ=7.51 (1H, s), 7.44 (1H, d), 7.34–7.29 (3H, m), 7.25–7.23 (2H, m), 7.15–7.12 (2H, m), 7.07 (1H, s), 6.77 (1H, d) 4.88 (1H, partially obscured by solvent), 4.65 (2H, s), 4.55 (2H, s), 3.61–3.56 (1H, m), 3.27–3.12 (3H, m), 2.88–2.82 (1H, m), 2.45 (3H, s), 1.27–1.26 (3H, d) ppm.

HRMS (ESI): m/z [M+H]$^+$ found 520.2245; requires 520.2265.

EXAMPLE 19

5-[(2R)-2-({(2R)-2-Hydroxy-2-(4-hydroxy-3-hydroxymethyl phenyl)ethyl}amino)propyl}-N-(2,3-dimethoxybenzyl)-1H-indole-2-carboxamide

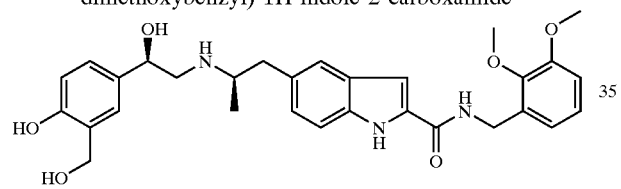

Prepared using the acid from Preparation 11 and the method described for Example 12.

$^1$H NMR (400 MHz, CD$_3$OD): δ=7.51 (1H, s), 7.44 (1H, d), 7.34 (1H, s), 7.15–7.12 (2H, m), 7.09 (1H, s), 7.05–6.99 (1H, m), 6.96–6.92 (2H, m), 6.77 (1H, d), 4.88 (1H, partially obscured by solvent), 4.65 (2H, s), 4.62 (2H, s), 3.86 (3H, s), 3.85 (3H, s), 3.61–3.55 (1H, m), 3.27–3.13 (3H, m), 2.88–2.82 (1H, m), 1.27–1.26 (3H, d) ppm.

HRMS (ESI): m/z [M+H]$^+$ found 534.2579; requires 534.2599.

EXAMPLE 20

5-[(2R)-2-({(2R)-2-Hydroxy-2-(4-hydroxy-3-hydroxymethyl phenyl)ethyl}amino)propyl}-N-(2,4-dimethoxybenzyl)-1H-indole-2-carboxamide

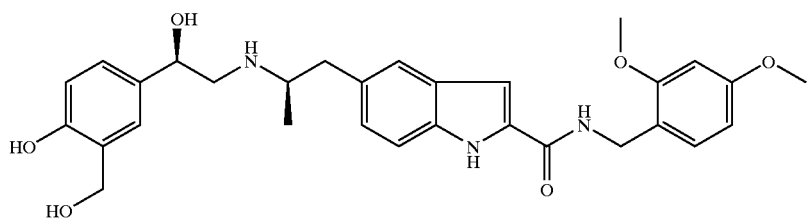

Prepared using the acid from Preparation 11 and the method described for Example 12.

$^1$H NMR (400 MHz, CD$_3$OD): δ=7.50 (1H, s), 7.43 (1H, d), 7.34 (1H, s), 7.19 (1H, d), 7.15–7.09 (2H, m), 7.07 (1H, s), 6.77 (1H, d), 6.55 (1H, s), 6.51–6.44 (1H, m), 4.89 (1H, partially obscured by solvent), 4.65 (2H, s), 4.51 (2H, s), 3.85 (3H, s), 3.78 (3H, s), 3.62–3.56 (1H, m), 3.27–3.13 (3H, m), 2.88–2.82 (1H, m), 1.27–1.26 (3H, d) ppm.

HRMS (ESI): m/z [M+H]$^+$ found 534.2577; requires 534.2599.

EXAMPLE 21

5-[(2R)-2-({(2R)-2-Hydroxy-2-(4-hydroxy-3-hydroxymethyl phenyl)ethyl}amino)propyl}-N-(2-ethoxybenzyl)-1H-indole-2-carboxamide

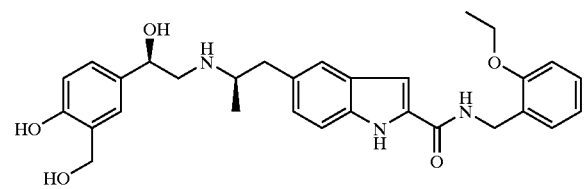

Prepared using the acid from Preparation 11 and the method described for Example 12.

$^1$H NMR (400 MHz, CD$_3$OD): δ=7.51 (1H, s), 7.44 (1H, d), 7.34 (1H, s), 7.28–7.20 (2H, m), 7.15–7.12 (2H, m), 7.09 (1H, s), 6.96–6.94 (1H, d), 6.91–6.87 (1H, t), 6.78 (1H,), 4.89 (1H, partially obscured by solvent), 4.65 (2H, s), 4.61 (2H, s), 4.10 (2H, q), 3.62–3.56 (1H, m), 3.27–3.13 (3H, m), 2.88–2.82 (1H, m), 1.44–1.40 (3H, t), 1.28–1.26 (3H, d) ppm.

HRMS (ESI): m/z [M+H]$^+$ found 518.2631; requires 518.2650.

EXAMPLE 22

5-[(2R)-2-({(2R)-2-Hydroxy-2-(4-hydroxy-3-hydroxymethyl phenyl)ethyl}amino)propyl}-N-benzyl-N-methyl-1 H-indole-2-carboxamide

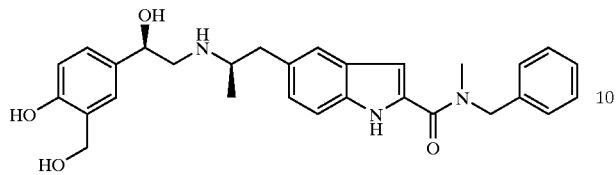

Prepared using the acid from Preparation 11 and the method described for Example 12.

¹H NMR (400 MHz, CD$_3$OD): δ=7.54–7.27 (9H, m), 7.14–7.12 (2H, m), 6.77 (1H, d), 5.08–4.92 (1H, m), 4.90 (2H, partially obscured by solvent), 4.64 (2H, s), 3.61–3.53 (1H, m), 3.28–3.05 (6H, m), 2.87–2.81 (1H, m), 1.26–1.25 (3H, d), ppm.

LRMS (APCI): m/z [M+H]$^+$ 488, [M–H]$^-$ 486.

EXAMPLE 23

[(2R)-2-({(2R)-2-Hydroxy-2-(4-hydroxy-3-hydroxymethyl phenyl)ethyl}amino)propyl}-N-benzyl-1H-indole-2-carboxamide

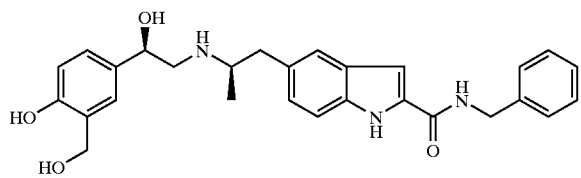

Prepared using the acid from Preparation 11 and the method described for Example 12.

¹H NMR (400 MHz, CD$_3$OD): δ=7.51 (1H, s), 7.44 (1H, d), 7.38–7.30 (5H, m), 7.26–7.23 (1H, m), 7.15–7.12 (2H, m), 7.08 (1H, s), 6.78–6.76 (1H, d), 4.88 (1H, partially obscured by solvent), 4.65 (2H, s), 4.59 (2H, s), 3.61–6.56 (1H, m), 3.27–3.13 (3H, m), 2.88–2.82 (1H, m), 1.27 (3H, s) ppm.

HRMS (ESI): m/z [M+H]$^+$ found 474.2370; requires 474.2388.

EXAMPLE 24

[(2R)-2-({(2R)-2-Hydroxy-2-(4-hydroxy-3-hydroxymethyl phenyl)ethyl}amino)propyl}-N-(4-fluorobenzyl)-1H-indole-2-carboxamide

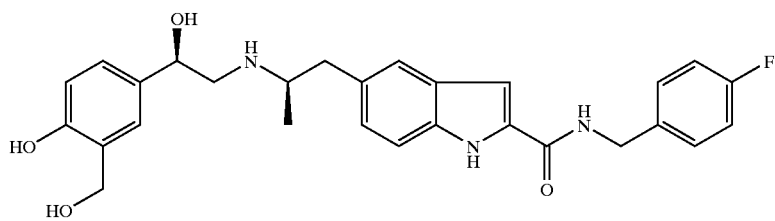

Prepared using the acid from Preparation 11 and the method described for Example 12.

¹H NMR (400 MHz, CD$_3$OD): δ=7.88 (1H, d), 7.74 (1H, d), 7.33–7.57 (7H, m), 7.13 (2H, m), 7.05 (2H, t), 6.77 (1H, d), 4.85 (1H, m), 4.65 (2H, s), 4.56 (2H, s), 3.54–3.62 (1H, m), 3.13–3.27 (3H, m), 2.81–2.88 (1H, m), 1.27 (3H, d) ppm.

HRMS (ESI): m/z [M+H]$^+$ found 492.2275; requires 492.2300.

EXAMPLE 25

5-[(2R)-2-({(2R)-2-Hydroxy-2-(4-hydroxy-3-hydroxymethyl phenyl)ethyl}amino)propyl}-N-(2-methoxy-3-methyl-benzyl)-1H-indole-2-carboxamide

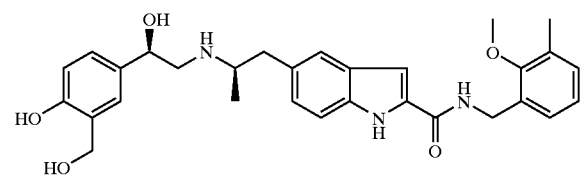

Prepared using the acid from Preparation 46 and the method described for Example 12.

¹H NMR (400 MHz, CD$_3$OD): δ=7.44 (1H, s), 7.38 (1H, d), 7.27(1H, s), 7.17 (1H, d), 7.12–7.05 (4H, m), 6.99 (1H, t), 6.70 (1H, d), 4.65 (2H, s), 4.61(3H, s), 3.80 (3H, s), 3.12–2.95(4H, m), 2.79 (1H, m), 2.30 (3H, s), 1.19 (3H, d) ppm.

HRMS (ESI): m/z [M+H]$^+$ found 518.2650, C$_{30}$H$_{36}$N$_3$O$_5$ requires 518.2646

EXAMPLE 26

5-[(2R)-2-({(2R)-2-Hydroxy-2-(4-hydroxy-3-hydroxymethyl phenyl)ethyl}amino)propyl}-N-(3-methoxy-2-methyl benzyl)-1H-indole-2-carboxamide

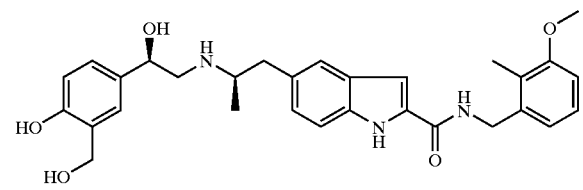

Prepared using the acid from Preparation 45 and the method described for Example 12.

¹H NMR (400 MHz, CD$_3$OD): δ=7.56 (2H, d), 7.15 (1H, d), 7.09 (1H, d), 7.01–6.95 (4H, m), 6.83 (1H, d), 6.60 (1H, d) 4.59 (2H, s), 4.55 (2H, s), 3.80 (3H, s), 3.01–2.95(2H, m), 2.80–2.62 (3H, m), 2.25 (3H, s), 1.13 (3H, d) ppm.
LRMS (ESI): m/z [M+H]$^+$ 518.63

EXAMPLE 27

1-Ethyl-5-[(2R)-2-({(2R)-2-hydroxy-2-(4-hydroxy-3-hydroxy methylphenyl)ethyl}amino)propyl}-N-(2,6-dimethoxybenzyl)-1H-indole-2-carboxamide

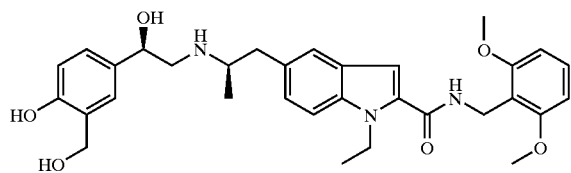

Prepared using the acid from Preparation 31 and the method described for Example 12.

$^1$H NMR (400 MHz, CD$_3$OD): δ=7.31–7.24 (3H, m), 7.16 (1H, bs), 7.02–6.96 (2H, m), 6.75–6.58 (4H, m), 4.64–4.50 (7H, m), 3.86 (6H, s), 2.99–2.91 (2H, m), 2.74–2.67 (3H, m), 1.33 (3H, t), 1.11 (3H, d) ppm.
LRMS (ESI): m/z [M+H]$^+$ 562, [M+Na]$^+$ 584.

EXAMPLE 28

1-Ethyl-5-[(2R)-2-({(2R)-2-hydroxy-2-(4-hydroxy-3-hydroxy methylphenyl)ethyl}amino)propyl}-N-(2-ethoxybenzyl)-1H-indole-2-carboxamide

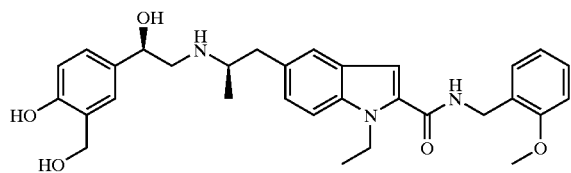

Prepared using the amide from Preparation 31 and the method described for Example 12.

$^1$H NMR (400 MHz, CD$_3$OD): δ=7.32–7.23 (4H, m), 7.16 (1H, bs), 7.03–6.89 (5H, m), 6.60 (1H, d), 4.61–4.50 (7H, m), 3.87 (3H, s), 2.96–2.89 (2H, m), 273–2.65 (3H, m), 1.32 (3H, t), 1.10 (3H, d) ppm.
LRMS (ESI): m/z [M+H]$^+$ 532, [M+Na]$^+$ 554.

EXAMPLE 29

1-Ethyl-5-[(2R)-2-({(2R)-2-hydroxy-2-(4-hydroxy-3-hydroxy methylphenyl)ethyl}amino)propyl}-N-(4-chlorobenzyl)-1H-indole-2-carboxamide

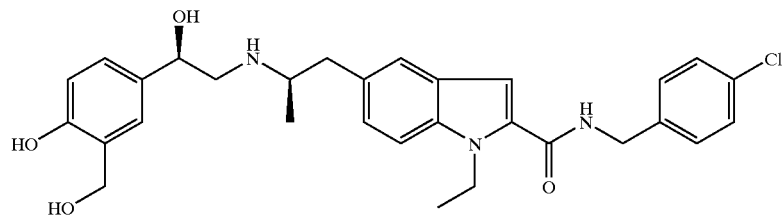

Prepared using the amide from Preparation 31 and the method described for Example 12.

$^1$H NMR (400 MHz, CD$_3$OD): δ=7.37–7.30 (6H, m), 7.16 (1H, bs), 7.04–7.01 (1H, m), 6.97–6.95 (2H, m), 6.60 (1H, d), 4.60–4.49 (7H, m), 2.96–2.88 (2H, m), 2.72–2.64 (3H, m), 1.32 (3H, t), 1.10 (3H, d) ppm.
LRMS (ESI): m/z [M+H]$^+$ 536, [M+Na]$^+$ 558.

EXAMPLE 30

1-Methyl-5-[(2R)-2-({(2R)-2-hydroxy-2-(4-hydroxy-3-hydroxy methylphenyl)ethyl}amino)propyl}-N-(2,6-dimethoxybenzyl)-1H-indole-2-carboxamide

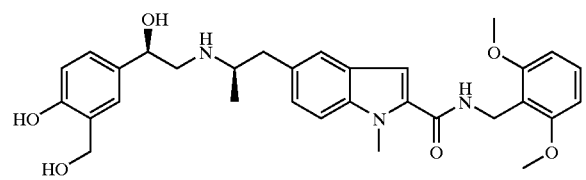

Prepared using the amide from Preparation 26 and the method described for Example 12.

$^1$H NMR (400 MHz, CD$_3$OD): δ=7.28–7.24 (3H, m), 7.13 (1H, bs), 7.00 (1H, d), 6.91 (1H, d), 6.77 (1H, s), 6.65 (2H, d), 6.53 (1H, d), 4.65 (2H, s), 4.59–4,56 (1H, m), 4.49 (2H, s), 3.96 (3H, s), 3.87 (6H, s), 2.98–2.92 (2H, m), 2.72–2.63 (3H, m), 1.11 (3H, m) ppm.
LRMS (ESI): m/z [M+H]$^+$ 548, [M+Na]$^+$ 570.

EXAMPLE 31

1-Methyl-5-[(2R)-2-({(2R)-2-hydroxy-2-(4-hydroxy-3-hydroxy methylphenyl)ethyl}amino)propyl}-N-(2-methoxybenzyl)-1H-indole-2-carboxamide

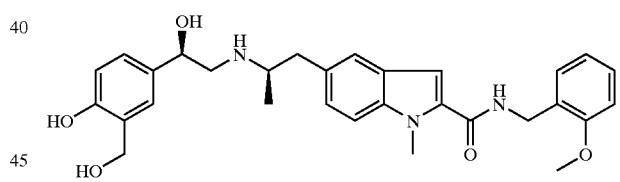

Prepared using the amide from Preparation 26 and the method described for Example 12.

$^1$H NMR (400 MHz, CD$_3$OD): δ=7.32–7.24 (4H, m), 7.12 (1H, bs), 7.02–6.89 (5H, m), 6.53 (1H, d), 4.58–4.53 (3H, m), 4.49 (2H, s), 3.97 (3H, s), 3.89 (3H, s), 2.95–2.88 (2H, m), 2.75–2.59 (3H, m), 1.12–1.10 (3H, m) ppm.
LRMS (ESI): m/z [M+H]$^+$ 518, [M+Na]$^+$ 540.

EXAMPLE 32

1-Methyl-5-[(2R)-2-({(2R)-2-hydroxy-2-(4-hydroxy-3-hydroxy methylphenyl)ethyl}amino)propyl}-N-(4-chlorobenzyl)-1H-indole-2-carboxamide

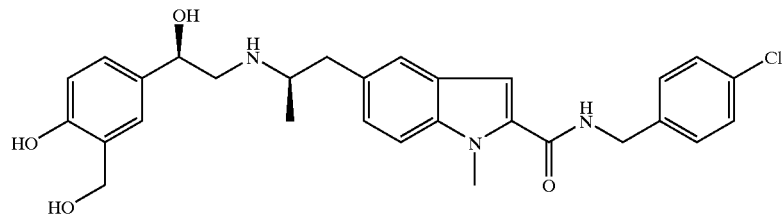

Prepared using the amide from Preparation 26 and the method described for Example 12.

$^1$H NMR (400 MHz, CD$_3$OD): δ=7.39–7.27 (6H, m), 7.11 (1H, bs), 7.02 (1H, d), 6.95 (1H, s), 6.91 (1H, d), 6.54 (1H, d), 4.57–4.54 (3H, m), 4.49 (2H, s), 3.99 (3H, s), 2.95–2.89 (2H, m), 2.77–2.60 (3H, m), 1.11 (3H, d) ppm.

LRMS (ESI): m/z [M+H]$^+$ 522, [M+Na]$^+$ 544

EXAMPLE 33

5-[(2R)-2-({(2R)-2-Hydroxy-2-(4-hydroxy-3-hydroxymethyl phenyl)ethyl}amino)butyl}-N-(2-methoxybenzyl)-1H-indole-2-carboxamide

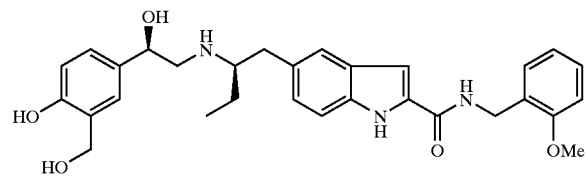

A solution of Preparation 40 (158 mg, 220 μmol) in ethanol (10 ml) was treated with ammonium formate (70 mg, 1.1 mmol) and palladium hydroxide on carbon (10 mg) and heated to reflux for 2 h. Ammonium fluoride (40 mg, 1.1 mmol) in water (1 ml) was then added and the resulting mixture stirred at 40° C. for 24 h. The solvents were then removed and the crude material taken up in ethyl acetate, washed with water (containing 1% 0.88 ammonia) and dried (Na$_2$SO$_4$). The product was purified by chromatography (2–5% MeOH in CH$_2$Cl$_2$ and 0.3% NH$_3$) to yield a colourless solid (66 mg).

$^1$H NMR (400 MHz, CD$_3$OD): δ=7.38–7.15 (5H, m), 7.04–6.88 (5H, m), 6.60–6.54 (1H, d), 4.59 (2H, s), 4.58–4.52 (3H, m), 3.86 (3H, s), 2.89–2.59 (5H, m), 1.61–1.39 (2H, m), 0.98–0.94 (3H, t) ppm.

LRMS (ESI): m/z [M+H]$^+$ 518, [M+Na]$^+$ 540.

EXAMPLE 34

5-[(2R)-2-({(2R)-2-Hydroxy-2-(4-hydroxy-3-hydroxymethyl phenyl)ethyl}amino)butyl}-N-(2,6-dimethoxybenzyl)-1H-indole-2-carboxamide

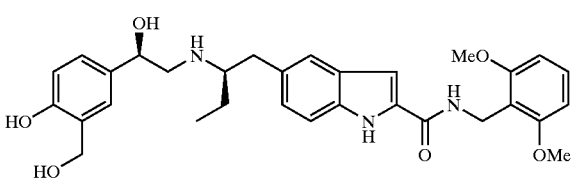

Prepared using the ether from Preparation 41 and the method described for Example 33.

$^1$H NMR (400 MHz, CD$_3$OD): δ=7.38–7.12 (4H, m), 6.98–6.90 (3H, m), 6.68–6.65 (2H, d), 6.58–6.56 (1H, d), 4.66 (2H, s), 4.58–4.53 (3H, m), 3.86 (6H, s), 2.88–2.59 (5H, m), 1.60–1.38 (2H, m), 0.98–0.93 (3H, t) ppm.

LRMS (ESI): m/z [M+H]$^+$ 548, [M+Na]$^+$ 570.

EXAMPLE 35

5-[(2R)-2-({(2R)-2-Hydroxy-2-(4-hydroxy-3-hydroxymethyl phenyl)ethyl}amino)butyl}-N-(2-ethoxybenzyl)-1H-indole-2-carboxamide

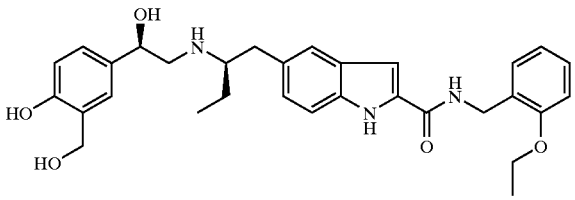

Prepared using the ether from Preparation 42 and the method described for Example 33.

$^1$H NMR (400 MHz, CD$_3$OD): δ=7.35–7.16 (5H, m), 7.04–6.88 (5H, m), 6.58–6.56 (1H, d), 4.61 (2H, s), 4.58–4.52 (3H, m), 4.15–4.06 (2H, q), 2.90–2.59 (5H, m), 1.62–1.40 (5H, m), 0.98–0.93 (3H, t) ppm.

LRMS (ESI): m/z [M+H]$^+$ 532, [M+Na]$^+$ 554.

EXAMPLE 36

5-[(2R)-2-({(2R)-2-Hydroxy-2-(4-hydroxy-3-hydroxymethyl phenyl)ethyl}amino)butyl}-N-benzyl-1H-indole-2-carboxamide

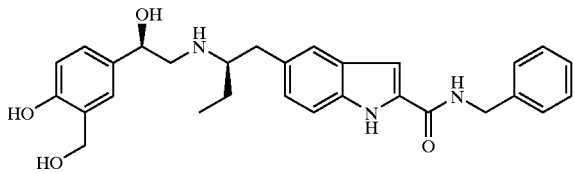

Prepared using the ether from Preparation 39 and the method described for Example 33.

$^1$H NMR (400 MHz, CD$_3$OD): δ=7.41–6.92 (11H, m), 6.58–6.56 (1H, d), 4.59 (2H, s), 4.57–4.51 (3H, m), 2.88–2.58 (5H, m), 1.62–1.38 (2H, m), 0.98–0.92 (3H, t) ppm.

LRMS (ESI): m/z [M+H]$^+$ 488, [M+Na]$^+$ 510.

The following Preparations describe the preparation of certain intermediates used in the preceding Examples.

Preparation 1

5-[(2R)-2-({(2R)-2-{[tert-butyl(dimethyl)silyl]oxy]-2-[4-hydroxy-3-(hydroxymethyl)phenyl]ethyl}amino)propyl]-N-(2-methoxy benzyl)-1H-indole-2-carboxamide

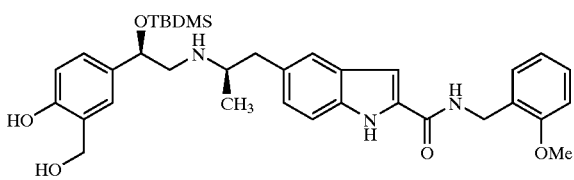

A solution of 5-[(2R)-2-({(2R)-2-{[tert-butyl(dimethyl)silyl]oxy}-2-[4-hydroxy-3-(hydroxymethyl)phenyl]ethyl}amino)propyl]-1H-indole-2-carboxylic acid (Preparation 5, 0.25 g, 0.50 mmol), 1-(3-dimethylaminopropyl)-3-ethylcarbodiimide hydrochloride (106 mg, 0.55 mmol), hydroxybenzotriazole (75 mg, 0.55 mmol) in N,N-dimethylformamide (5 ml) was treated with triethylamine (0.15 ml, 0.55 mmol) and 2-methoxybenzylamine (0.07 ml, 0.55 mmol) and the resulting suspension left to stir at room temperature under a nitrogen atmosphere for 18 hours. The solvent was removed in vacuo and the residue partitioned between dichloromethane (50 ml) and saturated aqueous sodium bicarbonate (20 ml). The organic phase was separated, dried (sodium sulphate) and the solvent removed in vacuo. The residue was purified by flash column chromatography on silica gel eluting with dichloromethane:methanol (95:5 changing to 90:10, by volume) to give the title compound as a colourless foam (76 mg).

$^1$H NMR (400 MHz, CD$_3$OD): δ=7.35–7.23 (4H, m), 7.16 (1H, s), 7.05 (1H, s), 7.01–6.89 (4H, m), 6.62–6.59 (1H, d), 4.70–4.67 (1H, t), 4.60–4.57 (4H, m), 3.89 (3H, s), 3.01–2.96 (1H, m), 2.93–2.88 (1H, m), 2.75–2.61 (3H, m), 1.11–1.10 (3H, d), 0.73 (9H, s), –0.08 (3H, s), –0.25 (3H, s) ppm.

LRMS (electrospray): m/z [M+H]$^+$ 618.

Analysis: Found C, 66.98; H, 7.67; N, 6.70; C$_{35}$H$_{47}$N$_3$O$_5$Si. 0.5H$_2$O requires C, 67.06; H, 7.72; N, 6.70.

Preparation 2

5-[(2R)-2-({(2R)-2-{[tert-butyl(dimethyl)silyl]oxy}-2-[4-hydroxy-3-(hydroxymethyl)phenyl]ethyl}amino)propyl]-N-[4-(trifluoro methyl)benzyl]-1H-indole-2-carboxamide

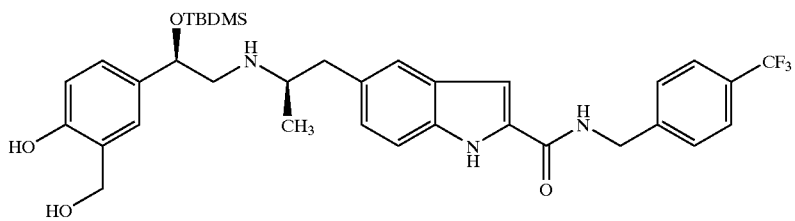

Prepared analogously to 5-[(2R)-2-({(2R)-2-{[tert-butyl(dimethyl)silyl]oxy}-2-[4-hydroxy-3-(hydroxymethyl)phenyl]ethyl}amino)propyl]-N-(2-methoxybenzyl)-1H-indole-2-carboxamide using 4-trifluoromethylbenzylamine to give the title compound as a pale brown foam.

$^1$H NMR (400 MHz, CD$_3$OD): δ=7.65–7.63 (2H, m), 7.57–7.55 (2H, m), 7.40–7.38 (2H, m), 7.21 (1H, s), 7.08–7.04 (2H, m), 6.99–6.97 (1H, d), 6.67–6.65 (1H, d), 4.80–4.77 (1H, m), 4.68 (2H, s), 4.64–4.57 (2H, m), 3.08–3.02 (2H, m), 2.86–2.78 (3H, m), 1.18–1.17 (3H, d), 0.74 (9H, s), –0.05 (3H, s), –0.23 (3H,s) ppm.

LRMS (electrospray): m/z [M+H]$^+$ 656.

Preparation 3

5-[(2R)-2-({(2R)-2-{[tert-butyl(dimethyl)silyl]oxy}-2-[4-hydroxy-3-(hydroxymethyl)phenyl]ethyl}amino)propyl]-N-(2,6-dimethoxy benzyl)-1H-indole-2-carboxamide

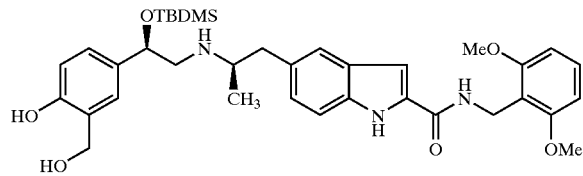

Prepared analogously to 5-[(2R)-2-({(2R)-2-{[tert-butyl(dimethyl)silyl]oxy}-2-[4-hydroxy-3-(hydroxymethyl)phenyl]ethyl}amino)propyl]-N-(2-methoxybenzyl)-1H-indole-2-carboxamide using 2,6-dimethoxybenzylamine to give the title compound as a pale yellow foam.

$^1$H NMR (400 MHz, CD$_3$OD): δ=7.35–7.28 (3H, m), 7.18 (1H, bs), 7.02–6.95 (3H, m), 6.71 (2H, d), 6.63 (1H, d), 4.70–4.68 (3H, m), 4.62–4.56 (2H, m), 3.90 (6H, s), 3.00–2.89 (2H, m), 2.72–2.62 (3H, m), 1.11 (3H, d), 0.76 (9H, s), –0.05 (3H, s), –0.22 (3H, s) ppm.

LRMS (electrospray): m/z [M+H]$^+$ 648, [M+Na]$^+$ 670.

Preparation 4

5-(2R)-2-({(2R)-2-{[tert-butyl(dimethyl)silyl]oxy}-2-[4-hydroxy-3-(hydroxymethyl)phenyl]ethyl}amino)propyl]-N-(3-methoxybenzyl)-1H-indole-2-carboxamide

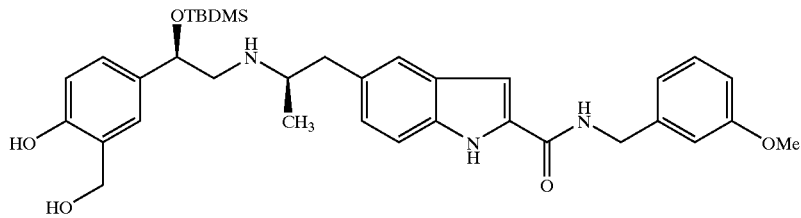

Prepared analogously to 5-[(2R)-2-({(2R)-2-{[tert-butyl(dimethyl)silyl]oxy}-2-[4-hydroxy-3-(hydroxymethyl)phenyl]ethyl}amino)propyl]-N-(2-methoxybenzyl)-1H-indole-2-carboxamide using 3-methoxybenzylamine to give the title compound as a pale brown foam.

$^1$H NMR (400 MHz, CD$_3$OD): δ=7.36–7.34 (2H, m), 7.25–7.21 (1H, t), 7.17 (1H, s), 7.05–7.00 (2H, m), 6.95–6.94 (3H, m), 6.82–6.80 (1H, m), 6.62–6.60 (1H, d), 4.71–4.68 (1H, m), 4.62–4.54 (4H, m), 3.77 (3H, s), 3.02–2.90 (2H, m), 2.73–2.64 (3H, m), 1.12–1.10 (3H, d), 0.71 (9H, s), −0.09 (3H, s), −0.26 (3H, s) ppm.

LRMS (electrospray): m/z [M+H]$^+$ 618.

Analysis: Found C, 66.45; H, 7.57; N, 6.63; C$_{35}$H$_{47}$N$_3$O$_5$Si. 0.85H$_2$O requires C, 66.39; H, 7.75; N, 6.64.

Preparation 5

5-[(2R)-2-({(2R)-2-{[tert-butyl(dimethyl)silyl]oxy}-2-[4-hydroxy-3-(hydroxymethyl)phenyl]ethyl}amino)propyl]-N-[2-(3-methoxyphenyl)ethyl]-1H-indole-2-carboxamide

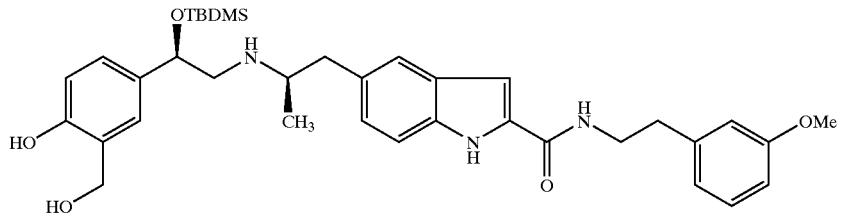

Prepared analogously to 5-[(2R)-2-({(2R)-2-{[tert-butyl(dimethyl)silyl]oxy}-2-[4-hydroxy-3-(hydroxymethyl)phenyl]ethyl}amino)propyl]-N-(2-methoxybenzyl)-1H-indole-2-carboxamide using 3-methoxyphenethylamine to give the title compound as a pale brown foam.

$^1$H NMR (400 MHz, CD$_3$OD): δ=7.35–7.33 (2H, m), 7.20–7.16 (2H, m), 7.02–6.99 (1H, m), 6.95–6.93 (2H, m), 6.84–6.83 (2H, m), 6.77–6.74 (1H, m), 6.63–6.61 (1H, d), 4.73–4.71 (1H, m), 4.62–4.55 (2H, m), 3.74 (3H, s), 3.62–3.59 (2H, t), 3.09–3.04 (1H, m), 2.98–2.85 (4H, m), 2.76–2.68 (2H, m), 1.13–1.12 (3H, d), 0.72 (9H, s), −0.08 (3H, s), −0.25 (3H, s) ppm.

LRMS (electrospray): m/z [M+H]$^+$ 632.

Preparation 6

5-[(2R)-2-({(2R)-2-{[tert-butyl(dimethyl)silyl]oxy}-2-[4-hydroxy-3-(hydroxymethyl)phenyl]ethyl}amino)propyl]-N-(2,4-dichloro benzyl)-1H-indole-2-carboxamide

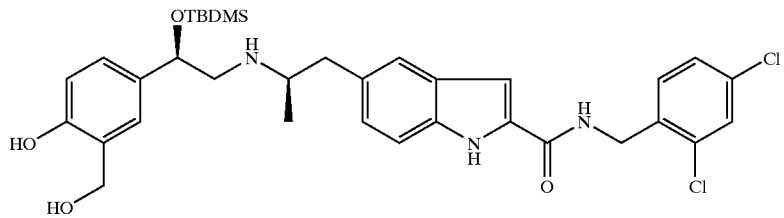

Prepared using the acid from Preparation 11 and the method described for Preparation 1.

¹H NMR (400 MHz, CD₃OD): δ=7.47 (1H, s), 7.42 (1H, m), 7.33–7.29 (3H, m), 7.15 (1H, s), 7.07 (1H, s), 7.00 (1H, d), 6.93 (1H, d), 6.60 (1H, d), 4.67 (13H, m), 4.60–4.53 (2H, m), 2.98 (1H, m), 2.90 (1H, m), 2.73 (2H, m), 2.63 (1H, m), 1.10 (3H, d), 0.72 (9H, s), −0.09 (3H, s), −0.26 (3H, s)

LRMS (APCI): m/z [M]⁺ 656.

Preparation 7

5-[(2R)-2-({(2R)-2-{[tert-butyl(dimethyl)silyl]oxy}-2-[4-hydroxy-3-(hydroxymethyl)phenyl]ethyl}amino)propyl]-N-(3-benzyloxy-2,6-dimethoxybenzyl)-1H-indole-2-carboxamide Preparation 7 (137 mg, 182 μmmol) was hydrogenated with palladium on carbon (10%, 20 mg) at 50 psi for 12 h at 30° C. The reaction mixture was filtered through a filter-aid and the solvent removed. The crude material was then purified by chromatography (0–7% MeOH in CH₂Cl₂ and 1% ammonia) to yield a clear glass (73 mg).

¹H NMR (400 MHz, CD₃OD): δ=−0.27 (3H, s), −0.10 (3H, s), 0.72 (9H, s), 1.09 (3H, m), 2.69 (3H, m), 3.13 (2H, m), 3.34 (3H, m), 3.81 (3H, s), 3.85 (3H, s), 4.56 (1H, d), 4.65 (2H, bs), 4.92 (3H, m), 6.59 (1H, d), 6.62 (1H, d), 6.80 (1H, d), 6.93 (1H, d), 6.97 (2H, s), 6.99 (1H, s), 7.15 (1H, s), 7.30 (2H, m) ppm.

LRMS (electrospray): m/z [M+H]⁺, 664, [M+Na]⁺, 696.

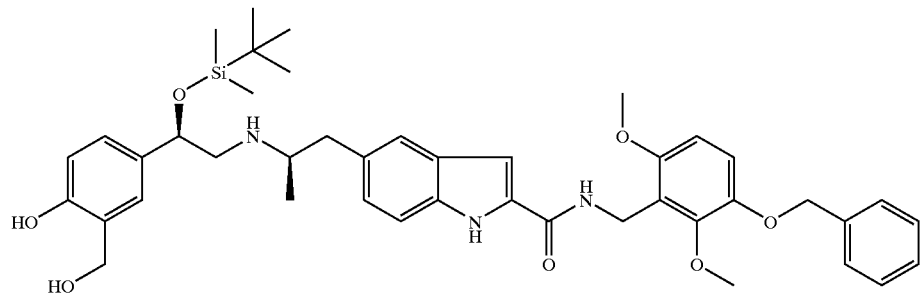

Prepared using the acid from Preparation 11, the amine from Preparation 59 and the method described for Preparation 1.

¹H NMR (400 MHz, CDCl₃): δ=−0.21 (3H, s), −0.05 (3H, s), 0.78 (9H, s), 110 (3H, bs), 2.55–2.95 (3H, m), 3.85 (3H, s), 3.98 (3H, s), 4.60 (3H, s), 4.78 (2H, d), 5.10 (2H, s), 6.50–6.70 (3H, m), 6.78–6.98 (5H, m), 7.27–7.43 (6H, m), 9.15 (1H, s).

LRMS (electrospray): m/z [M+H]⁺, 754, [M+Na]⁺, 776.

Preparation 8

5-[(2R)-2-({(2R)-2-{[tert-butyl(dimethyl)silyl]oxy}-2-[4-hydroxy-3-(hydroxymethyl)phenyl]ethyl}amino)propyl]-N-(3-hydroxy-2,6-dimethoxybenzyl)-1H-indole-2-carboxamide

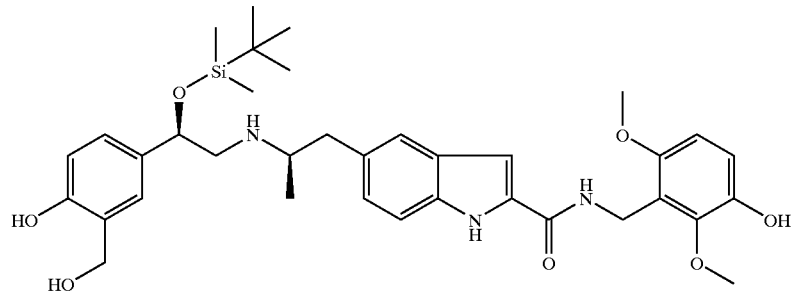

Preparation 9

5-[(2R)-2-({(2R)-2-{[tert-butyl(dimethyl)silyl]oxy}-2-[4-hydroxy-3-(hydroxymethyl)phenyl]ethyl}amino)propyl]-N-(4-benzyloxy-2,6-dimethoxybenzyl)-1H-indole-2-carboxamide

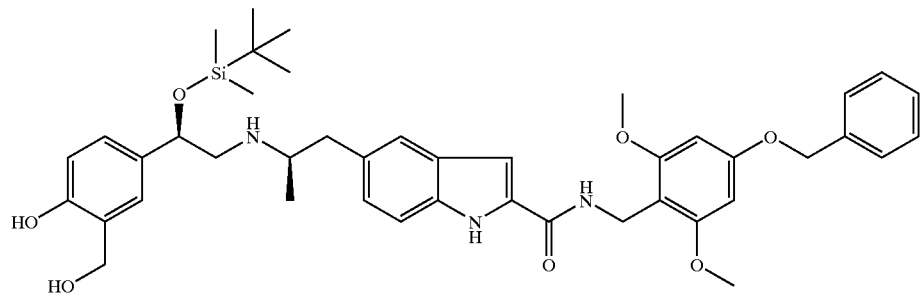

Prepared using the acid from Preparation 11, the amine from Preparation 49 and the method described for Preparation 1.

$^1$H NMR (400 MHz, CDCl$_3$): δ=−0.24 (3H, s), −0.07 (3H, s), 0.75 (9H, s), 1.06 (3H, d), 2.53 (1H, m), 2.68 (2H, m), 2.86 (2H, m), 3.83 (6H, s), 4./60 (3H, bs), 4.69 (2H, d), 5.06 (2H, s), 6.23 (2H, s), 6.60 (3H, m), 6.76 (1H, s), 6.93 (2H, t), 7.26 (1H, m), 7.33–7.45 (6H, m), 9.38 (1H, s) ppm.

LRMS (electrospray): m/z [M+H]$^+$, 754, [M+Na]$^+$, 776.

Preparation 10

5-[(2R)-2-({(2R)-2-{[tert-butyl(dimethyl)silyl]oxy}-2-[4-hydroxy-3-(hydroxymethyl)phenyl]ethyl}amino)propyl]-N-(2-benzyloxy-6-methoxybenzyl)-1H-indole-2-carboxamide

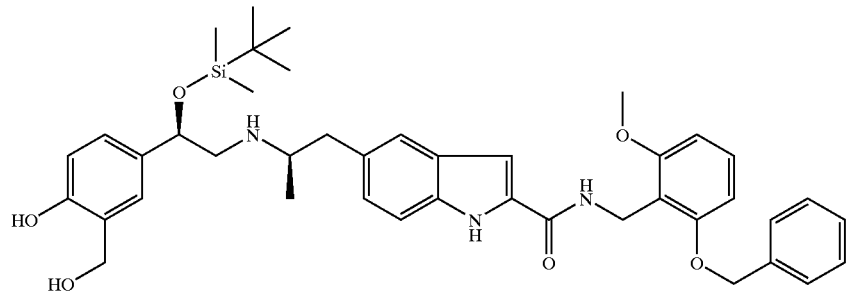

Prepared using the acid from Preparation 11, the amine from Preparation 52 and the method described for Preparation 1.

$^1$H NMR (400 MHz, CDCl$_3$): δ=−0.23 (3H, s), −0.06 (3H, s), 0.76 (9H, s), 1.07 (3H, d), 2.54 (1H, m), 2.68 (2H, m), 2.86 (2H, m), 3.38 (3H, s), 4.60 (1H, s), 4.84 (2H, s), 5.15 (2H, s), 6.43 (1H, s), 6.60 (1H, t), 6.67 (1H, d), 6.76 (1H, d), 6.82 (1H, t), 6.94 (2H, d), 7.23 (2H, m), 7.34–7.41 (3H, m), 7.48 (2H, m), 9.26 (1H, s) ppm.

LRMS (electrospray): m/z [M+H]$^+$, 724, [M+Na]$^+$, 746.

Preparation 11

5-[(2R)-2-({(2R)-2-{[tert-butyl(dimethyl)silyl]oxy}-2-[4-hydroxy-3-(hydroxymethyl)phenyl]ethyl}amino)propyl]-1H-indole-2-carboxylic acid

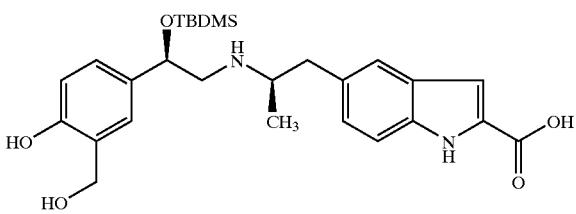

A solution of methyl 5-[(2R)-2-({(2R)-2-{[tert-butyl(dimethyl)silyl]oxy}-2-[4-hydroxy-3-(hydroxymethyl)phenyl]ethyl}amino)propyl]-1H-indole-2-carboxylate (Preparation 12, 0.30 g, 0.59 mmol) in 1,4-dioxane (10 ml) was treated with a solution of sodium hydroxide (59 mg, 1.46 mmol) in water (1 ml) and the resulting mixture left to stir at room temperature for 30 minutes. After this time the reaction mixture was heated to 90° C. for 30 minutes and then cooled to room temperature. The solvent was removed in vacuo and the residue re-dissolved in water (20 ml) and pH adjusted to 7 by addition of 2N Hydrochloric acid. The solid that formed was filtered off, solubilised in a mixture of dichloromethane and methanol (20 ml 90:10 by volume), dried (magnesium sulphate) and the solvent removed in vacuo to give the title compound as a pale orange foam.

$^1$H NMR (400 MHz, CD$_3$OD): δ=7.47–7.42 (2H, m), 7.27 (1H, s), 7.11–7.03 (3H, m), 6.76–6.74 (1H, d), 4.99–4.97

(1H, m), 4.67–4.58 (2H, m); 3.60–3.55 (1H, m), 3.28–3.26 (1H, m), 3.16–3.12 (1H, m), 3.09–3.04 (1H, m), 2.94–2.88 (1H, m), 1.28–1.26 (3H, d), 0.74 (9H, s), −0.03 (3H, s), −0.22 (3H, s) ppm.

LRMS (electrospray): m/z [M+H]$^+$, 499.

Preparation 12

Methyl 5-[(2R)-2-({(2R)-2-{[tert-butyl(dimethyl) silyl]oxy}-2-[4-hydroxy-3-(hydroxymethyl)phenyl] ethyl}amino)propyl]-1H-indole-2-carboxylate

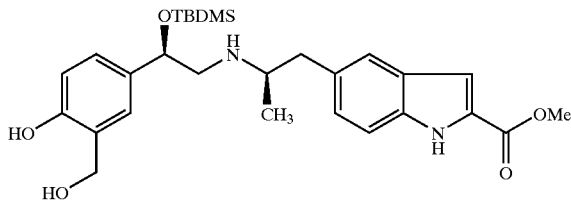

A suspension of methyl 5-{(2R)-2-[((2R)-2-[4-(benzyloxy)-3-(hydroxymethyl)phenyl]-2-{[tert-butyl (dimethyl)silyl]oxy}ethyl)amino]propyl}-1H-indole-2-carboxylate (Preparation 13, 0.38 g, 0.63 mmol) and 10% palladium on carbon (78 mg) in ethanol (20 ml) was stirred under an atmosphere of hydrogen (60 psi) at room temperature for 16 hours. The catalyst was filtered off through arbocel and the solvent removed in vacuo to give the title compound as a pale pink foam (316 mg), which was used without further purification.

$^1$H NMR (400 MHz, CD$_3$OD): δ=7.36–7.32 (2H, m), 7.15 (1H, bs), 7.09 (1H, b), (2H, 7.05–7.04 (1H, m), 6.95–6.93 (1H, m), 6.62 (1H, d), 4.69–4.66 (1H, m), 4.57 (2H, s), 3.92 (3H, s), 2.98–2.85 (2H, m), 2.70 (2H, d), 2.63–2.59 (1H, m), 1.08 (3H, d), 0.71 (9H, s), −0.09 (3H, s), −0.26 (3H, s) ppm.

LRMS (electrospray): m/z [M+H]$^+$ 513, [M+Na]$^+$ 535.

Analysis: Found C, 64.89; H, 7.93; N, 5.08; C$_{28}$H$_{40}$N$_2$O$_5$Si. 0.25H$_2$O requires C, 65.02; H, 7.89; N, 5.42

Optical Rotation [α]$^D_{25}$=−84.02° 0.4 mg/ml MeOH 635 nm

Preparation 13

Methyl 5-{(2R)-2-[((2R)-2-[4-(benzyloxy)-3-(hydroxymethyl)phenyl]-2-{[tert-butyl(dimethyl) silyl]oxy}ethyl)amino]propyl}-1H-indole-2-carboxylate

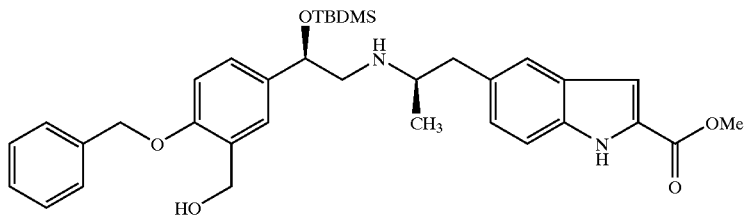

A solution of methyl 5-[(2R)-2-aminopropyl]-1H-indole-2-carboxylate (Preparation 14, 5.00 g, 21.5 mmol) and [2-(benzyloxy)-5-((1R)-2-bromo-1-{[tert-butyl(dimethyl) silyl]oxy}ethyl)phenyl]methanol (Preparation 20, 4.86 g, 10.8 mmol) in dichloromethane (50 ml) was heated to 90° C. allowing the dichloromethane to evaporate gradually. The resulting melt was left at 90° C. for 16 h under nitrogen. The reaction mixture was then cooled to room temperature and the resulting solid triturated with dichloromethane. The solid was filtered off and the solvent removed in vacuo to give a pale orange oil. The residue was purified by flash column chromatography on silica gel eluting with dichloromethane:methanol:0.88 ammonia (99:1:0.1 by volume) to give the title compound as a pale yellow oil (3.90 g).

$^1$H NMR (400 MHz, CD$_3$OD): δ=7.44–7.27 (8H, m), 7.08–7.04 (2H, m), 6.96–6.93 (1H, m), 6.67 (1H, d), 4.98 (2H, s), 4.72–4.67 (1H, m), 4.60 (2H, s), 3.82 (3H, s), 2.99–2.89 (2H, m), 2.77–2.72 (1H, m), 2.65–2.59 (2H, m), 1.11 (3H, d), 0.74 (9H, s), −0.07 (3H, s), −0.24 (3H, s) ppm.

LRMS (electrospray): m/z [M+H]$^+$ 603, [M+Na]$^+$ 625.

Analysis: Found C, 69.26; H, 7.72; N, 4.61; C$_{35}$H$_{46}$N$_2$O$_5$Si. 0.2H$_2$O requires C, 69.32; H, 7.71; N, 4.62

Preparation 14

Methyl 5-[(2R)-2-aminopropyl]-1H-indole-2-carboxylate

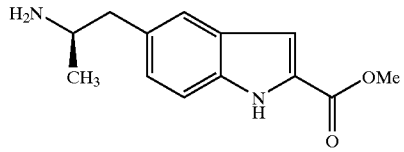

A solution of methyl 5-((2R)-2-{[(1R)-1-phenylethyl]amino}propyl)-1H-indole-2-carboxylate (Preparation 15, 9.34 g, 25.0 mmol) in ethanol (125 ml) was treated with ammonium formate (7.90 g, 125 mmol) and palladium hydroxide on carbon (2.81 g, 20% b/w palladium). The resulting suspension was purged with nitrogen and then heated to reflux for an hour. The reaction mixture was cooled to room temperature and filtered through arbocel to remove catalyst residues. The filtrate was reduced in vacuo and the residue was partitioned between 0.88 ammonia (100 ml) and dichloromethane (100 ml). The organic phase was separated and the aqueous extracted with more dichloromethane (100 ml). The combined organic extracts were dried (sodium sulphate) and the solvent removed in vacuo to give the title compound as a colourless oil (6.25 g, trace solvent remaining by $^1$H NMR).

$^1$H NMR (400 MHz, CD$_3$OD): δ=7.44 (1H, bs), 7.36 (1H, d), 7.13 (1H, d), 7.11 (1H, s), 3.90 (3H, s), 3.17–3.07 (1H, m), 2.77–2.61 (2H, m), 1.10 (3H, d) ppm LRMS (electrospray): m/z [M+H]$^+$ 233, [M+Na]$^+$ 255.

Optical Rotation [α]$^D_{25}$=−22.58° 6.76 mg/ml MeOH 589 nm

Preparation 15

Methyl 5-((2R)-2-{[(1R)-1-phenylethyl]amino}propyl)-1H-indole-2-carboxylate

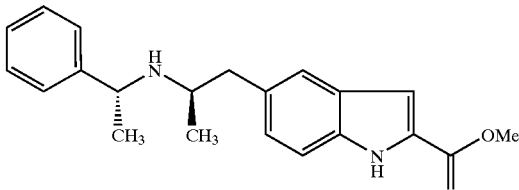

A solution of 1-tert-butyl 2-methyl 5-((2R)-2-{[(1R)-1-phenylethyl]amino}propyl)-1H-indole-1,2-dicarboxylate (Preparation 16, 20.48 g, 46.9 mmol) was treated with 4M hydrogen chloride in methanol and the resulting solution left to stir at room temperature for 16 hours and then heated at 50° C. for a further 2 hours. The solvent was removed in vacuo to give a solid which was crystallised from a mixture of methanol (125 ml) and diisopropylether (50 ml) to give the title compound as a colourless crystalline solid (9.34 g, d.e.>98% as determined by $^1$H NMR).

$^1$H NMR (400 MHz, CD$_3$OD): δ=7.53–7.49 (5H, m), 7.40–7.38 (2H, m), 7.10, 1H, bs), 6.97 (1H, bd), 4.61 (1H, q), 3.91 (3H, s), 3.42–3.37 (1H, m), 3.26–3.19 (1H, m), 2.72–2.66 (1H, m), 1.69 (3H, d), 1.19 (3H, d) ppm.

LRMS (electrospray): m/z [M+H]$^+$ 337.

Preparation 16

1-tert-butyl 2-methyl 5-((2R)-2-{[(1R)-1-phenylethyl]amino}propyl)-1H-indole-1,2-dicarboxylate

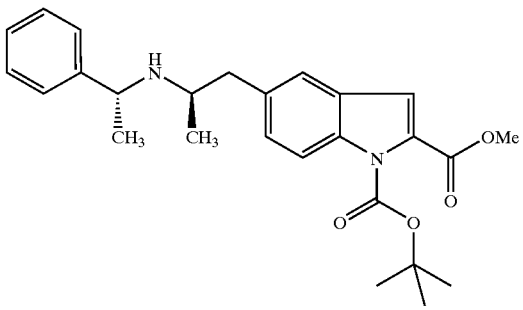

A solution of 1-tert-butyl 2-methyl 5-(2-oxopropyl)-1H-indole-1,2-dicarboxylate (18.0 g, 54.32 mmol), (R)-α-methyl benzylamine (Preparation 17, 6.4 ml, 49.65 mmol), sodium triacetoxyborohydride (15.80 g, 74.55 mmol) and acetic acid (3.0 ml, 52.38 mmol) in dichloromethane (500 ml) was stirred at room temperature for 16 hours. The reaction mixture was quenched by addition of saturated aqueous sodium bicarbonate (200 ml) and allowed to stir until effervescence ceased. The organic phase was separated and the aqueous phase extracted with further dichloromethane (100 ml). The combined organic extracts were dried (magnesium sulphate) and the solvent removed in vacuo. The residue was purified by flash column chromatography on silica gel eluting with dichloromethane:methanol:0.88 ammonia (99:1:0.1 changing to 98:2:0.2, by volume) to give a 4:1 mixture of diastereomers (R,R major) as a pale yellow oil (20.48 g).

$^1$H NMR (400 MHz, CD$_3$OD): δ=7.97–7.92 (1H, m), 7.41–7.02 (8H, m), 4.04–3.99 (1H, m), 3.96–3.94 (3H, m), 3.15–3.10 (1H, m), 2.80–2.70 (1H, m), 2.53–2.48 (1H, m), 1.66 (9H, s), 1.39–1.31 (3H, 2d), 1.10–0.95 (3H, 2d) ppm.

LRMS (electrospray): m/z [M+H]$^+$ 437.

Preparation 17

1-tert-butyl 2-methyl 5-(2-oxopropyl)-1H-indole-1,2-dicarboxylate

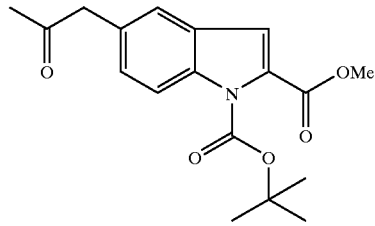

A solution of 1-tert-butyl 2-methyl 5-bromo-1H-indole-1,2-dicarboxylate (Preparation 18, 12.5 g, max 32.04 mmol), tributyltin methoxide (11.0 ml, 38.2 mmol), isoprenylacetate (5.3 ml, 48.1 mmol), palladium acetate (0.36 g, 5 mol %), tri-o-tolylphosphine (0.97 g, 10 mol %) in toluene (40 ml) was degassed and then heated at 100° C. for 8 hours. The reaction mixture was diluted with ethyl acetate (50 ml), 4M potassium fluoride (aqueous, 100 ml) and left to stir at room temperature overnight. The resulting mixture was filtered through arbocel washing the precipitate thoroughly with ethyl acetate (100 ml) and the organic phase of the filtrate separated, dried (magnesium sulphate) and the solvent removed in vacuo. The residue was purified by flash column chromatography on silica gel eluting with pentane:ethyl acetate (95:5 changing to 90:10, by volume) to give the title compound (8.2 g) as a yellow oil.

$^1$H NMR (400 MHz, CDCl$_3$): δ=8.05 (1H, d), 7.44 (1H, s), 7.25 (1H, d), 7.05 (1H, s), 3.92 (3H, s), 3.78 (2H, s), 2.16 (3H, s), 1.61 (9H, s) ppm.

LRMS (electrospray): m/z [M−H]$^-$ 330, [M+Na]$^+$ 354.

Preparation 18

1-tert-butyl 2-methyl 5-bromo-1H-indole-1,2-dicarboxylate

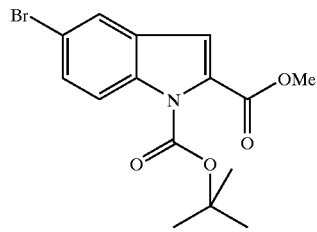

A solution of methyl 5-bromo-1H-indole-2-carboxylate (Preparation 19, 8.14 g, 32.04 mmol) in tetrahydrofuran (300 ml) was added to sodium hydride (1.35 g of a 40% dispersion in mineral oil, 33.7 mmol) at 0° C. under nitrogen. The resulting mixture was left to stir until effervescence ceased (50 minutes). A solution of di-tert-butyldicarbonate in further tetrahydrofuran (30 ml) was added to the reaction and the resulting mixture stirred vigorously, warming gradually to room temperature overnight. The solvent was removed in vacuo and the residue partitioned between ethyl acetate (200 ml) and water (200 ml). The organic phase was separated and the aqueous extracted with more ethyl acetate (2-fold 200 ml). The combined organics were dried (magnesium sulphate) and the solvent removed in vacuo to give the title compound as a pale yellow oil (12.5 g-trace solvent remaining).

$^1$H NMR (400 MHz, CDCl$_3$): δ=7.98 (1H, d), 7.74 (1H, s), 7.50 (1H, dd), 7.00 (1H, s), 3.92 (3H, s), 1.61 (9H, s) ppm.

LRMS (electrospray): m/z [M+H]$^+$ 352/354, [M+Na]$^+$ 376/378.

Preparation 19

Methyl 5-bromo-1H-indole-2-carboxylate

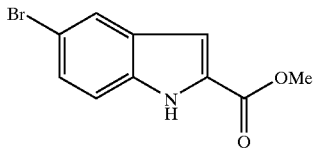

A solution of 5-Bromo-1H-indole-2-carboxylic acid (commercial, 10.0 g, 41.6 mmol) in methanol (200 ml) was cooled to 0° C. and saturated with HCl(g). The resulting solution was allowed to warm gradually to room temperature overnight. The solvent was removed in vacuo and the residue treated with 0.88 ammonia (500 ml). The resulting solution was extracted with dichloromethane (3-fold 150 ml) and the combined organics dried (magnesium sulphate) and the solvent removed in vacuo to give the required product as a colourless oil (8.35 g).

$^1$H NMR (400 MHz, CDCl$_3$): δ=8.96 (1H, bs), 7.83 (1H, s), 7.40 (1H, d), 7.30 (1H, d), 7.14 (1H, s), 3.95 (3H, s) ppm.

LRMS (electrospray): m/z [M−H]$^-$ 252/254.

Preparation 20

[2-(benzyloxy)-5-((1R)-2-bromo-1-{[tert-butyl (dimethyl)silyl]oxy}ethyl) phenyl]methanol

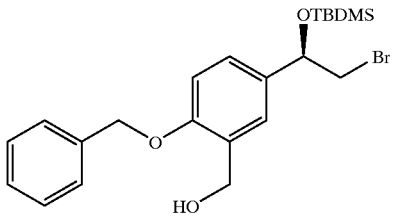

Borane methylsulfide complex (42.4 ml of ~10M solution, 424 mmol) was added drop wise to a solution of methyl 2-(benzyloxy)-5-((1R)-2-bromo-1-{[tert-butyl (dimethyl) silyl]oxy}ethyl)benzoate (Preparation 21, 91.0 g) in tetrahydrofuran (1600 ml). The resulting mixture was then heated to reflux for 2 hours and then cooled to 0° C. before quenching with methanol (270 ml). The mixture was left to stir, at room temperature for 16 hours and then the solvent removed in vacuo. The residue was partitioned between dichloromethane (500 ml) and water (500 ml). The aqueous phase was separated and extracted with more dichloromethane (500 ml) and the combined organic extracts washed with saturated aqueous sodium chloride (500 ml), dried (magnesium sulphate) and the solvent removed in vacuo. The residue was purified by flash column chromatography on silica gel eluting with cyclohexane:ethyl acetate (100:0 changing to 80:20, by volume) to give the title compound (68.7 g) as a colourless oil.

$^1$H NMR (400 MHz, CDCl$_3$): δ=7.42–7.36 (5H, m), 7.29–7.25 (3H, m), 6.94 (1H, d), 5.12 (2H, s), 4.84–4.81 (1H, m), 4.74 (2H, s), 3.48–3.40 (2H, m), 0.90 (9H, s), 0.11 (3H, s), −0.07 (3H, s) ppm.

LRMS (electrospray): m/z [M+Na]$^+$ 473/475.

Preparation 21

Methyl 2-(benzyloxy)-5-((1R)-2-bromo-1-{[tert-butyl(dimethyl)silyl]oxy}ethyl)benzoate

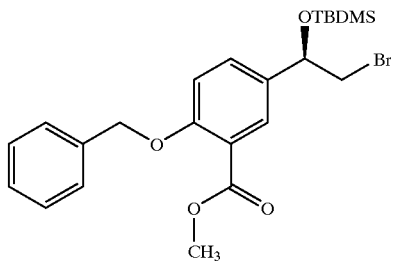

A solution of methyl 2-(benzyloxy)-5-[(1R)-2-bromo-1-hydroxyethyl]benzoate (71.05 g, 195 mmol), imidazole (18.52 g, 272 mmol), tert-butyldimethylsilyl chloride (32.23 g, 214 mmol) and 4-(dimethylamino)pyridine (0.44 g, 3.6 mmol) in DMF (270 ml) was left to stir at room temperature under a nitrogen atmosphere for a period of 24 hours. The solvent was removed in vacuo and the residue partitioned between ethyl acetate (500 ml) and water (500 ml). The organic phase was separated and washed with 2N hydrochloric acid (2-fold 500 ml), saturated aqueous sodium bicarbonate (2-fold 500 ml) saturated sodium chloride (500 ml), dried (magnesium sulphate) and the solvent removed in vacuo to give the title compound as a colourless oil (91.0 g).

$^1$H NMR (400 MHz, CDCl$_3$): δ=7.81 (1H, bs), 7.51–7.30 (6H, m), 7.01 (1H, d), 5.19 (2H, s), 4.85–4.82 (1H, m), 3.91 (3H, s), 3.48–3.39 (2H, m), 0.90 (9H, s), 0.11 (3H, s), −0.08 (3H, s) ppm.

LRMS (electrospray): m/z [M+Na]$^+$ 501/503.

Preparation 22

Ethyl 1-methyl-5-((2R)-2-{[(1R)-1-Phenylethyl] amino}propyl)-1H-indole-2-carboxylate

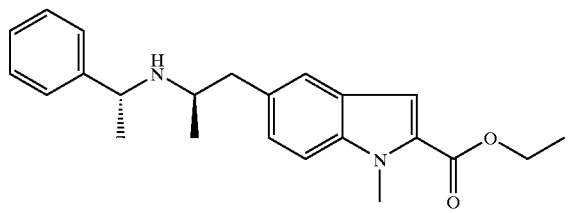

Prepared using the procedure of Preparation 15.

$^1$H NMR (400 MHz, CD$_3$OD): δ=7.56–7.48 (5H, m), 7.43–7.40 (2H, m), 7.19 (1H, s), 7.04 (1H, d), 4.62 (1H, q), 4.35 (2H, q), 4.03 (3H, s), 3.45–3.40 (1H, m), 3.28–3.21 (1H, m), 2.74–2.69 (1H, m), 1.70 (3H, d), 1.39 (3H, t), 1.19 (3H, d) ppm.

LRMS (ESI): m/z [M+H]⁺ 635, [M+Na]⁺ 387.

Preparation 23

Ethyl 1-methyl-5-[(2R)-2-aminopropyl]-1H-indole-2-carboxylate

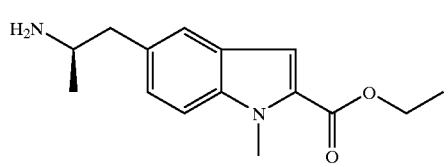

Prepared using the amine from Preparation 22 and the method described for Preparation 14.

¹H NMR (400 MHz, CD₃OD): δ=7.46–7.40 (2H, m), 7.22–7.19 (2H, m), 4.35 (2H, q), 4.04 (3H, s), 3.18–3.10 (1H, m), 2.77–2.65 (2H, m), 1.39 (3H, t), 1.10 (3H, d) ppm.

LRMS (ESI): m/z [M+H]⁺ 261, [M+Na]⁺ 283.

Preparation 24

Ethyl 1-methyl-5-{(2R)-2-[((2R)-2-[4-(benzyloxy)-3-(hydroxy methyl) phenyl]-2-{[tert-butyl(dimethyl)silyl]oxy}ethyl)amino]propyl}-1H-indole-2-carboxylate

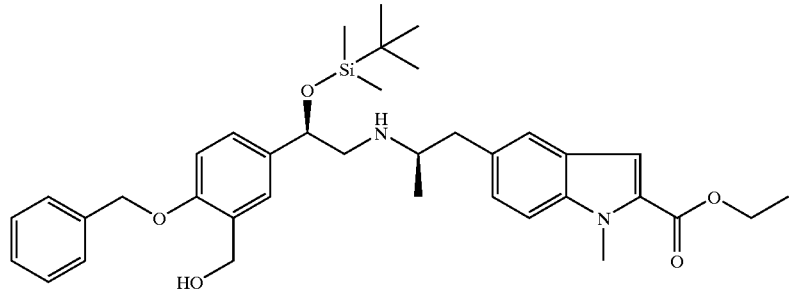

Prepared using the amine from Preparation 23, and the bromide from preparation 21 and the method described for Preparation 14.

¹H NMR (400 MHz, CD₃OD): δ=7.43–7.26 (8H, m), 7.18 (1H, bs), 7.10 (1H, d), 6.98 (1H, d), 6.72 (1H, d), 4.99 (2H, s), 4.71–4.68 (1H, m), 4.58 (2H, s), 4.29 (2H, q), 4.01 (3H, s), 2.98–2.90 (2H, m), 2.78–2.73 (1H, m), 2.65–2.58 (2H, m), 1.36 (3H, t), 1.11 (3H, d), 0.73 (9H, s), −0.07 (3H, s), −0.24 (3H, s) ppm.

LRMS (ESI): m/z [M+H]⁺ 631, [M+Na]⁺ 653.

Preparation 25

Ethyl 1-methyl-5-[(2R)-2-({(2R)-2-{[tert-butyl(dimethyl)silyl]oxy}-2-[4-hydroxy-3-(hydroxymethyl)phenyl]ethyl}amino)propyl]-1H-indole-2-carboxylate

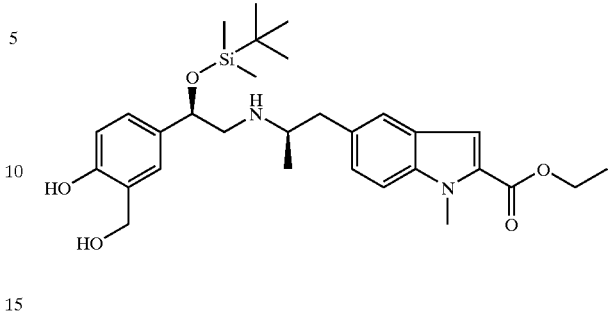

Prepared using the ester from Preparation 24 and the method described for Preparation 12.

¹H NMR (400 MHz, CD₃OD): δ=7.35–7.31 (2H, m), 7.18 (1H, s), 7.11–7.06 (2H, m), 6.92 (1H, d), 6.58 (1H, d), 4.66–4.63 (1H, m), 4.53 (2H, s), 4.37 (2H, q), 4.05 (3H, s), 2.96–2.87 (2H, m), 2.76–2.56 (3H, m), 1.40 (3H, t), 1.10 (3H, d), 0.72 (9H, s), −0.08 (3H, s), −0.26 (3H, s) ppm.

LRMS (ESI): m/z [M+H]⁺ 541, [M+Na]⁺ 563.

Preparation 26

1-Methyl-5-[(2R)-2-({(2R)-2-{[tert-butyl(dimethyl)silyl]oxy}-2-[4-hydroxy-3-(hydroxymethyl)phenyl]ethyl}amino)propyl]-1H-indole-2-carboxylic acid

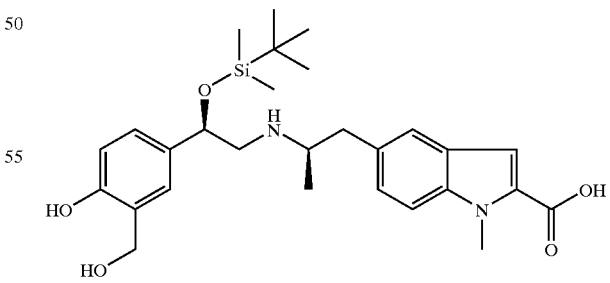

Prepared using the ester from Preparation 25 and the method described for Preparation 11.

¹H NMR (400 MHz, CD₃OD): δ=7.44–7.39 (2H, m), 7.25 (1H, s), 7.16–7.00 (3H, m), 6.72 (1H, d), 4.99–4.96 (1H, m), 4.64–4.56 (2H, m), 4.02 (3H, s), 3.60–3.54 (1H, m), 3.13–2.89 (4H, m), 1.27–1.26 (3H, m), 0.72 (9H, s), −0.04 (3H, s), −0.24 (3H, s) ppm.

LRMS (ESI): m/z [M+H]⁺ 513, [M+Na]⁺ 535.

Preparation 27

Ethyl 1-ethyl-5-((2R)-2-{[(1R)-1-phenylethyl]amino}propyl)-1H-indole-2-carboxylate

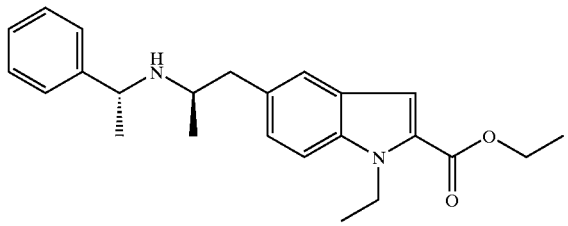

Prepared using the procedure of Preparation 15.

$^1$H NMR (400 MHz, CD$_3$OD): δ=7.57–7.45 (7H, m), 7.24 (1H, s), 7.07 (1H, d), 4.68–4.63 (3H, m), 4.40 (2H, q), 3.52–3.44 (1H, m), 3.29–3.25 (1H, m), 2.78–2.72 (1H, m), 1.74 (3H, d), 1.44 (3H, t), 1.37 (3H, t), 1.24 (3H, d) ppm.

LRMS (ESI): m/z [M+H]$^+$ 379, [M+Na]$^+$ 401.

Preparation 28

Ethyl 1-ethyl-5-[(2R)-2-aminopropyl]-1H-indole-2-carboxylate

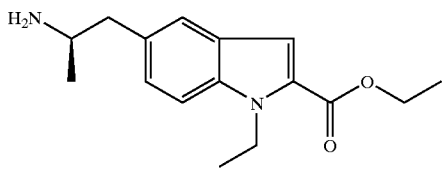

Prepared using the amine from Preparation 27 and the method described for Preparation 14.

$^1$H NMR (400 MHz, CD$_3$OD): δ=7.46–7.41 (2H, m), 7.20–7.18 (2H, m), 4.61 (2H, q), 4.35 (2H, q), 3.17–3.09 (1H, m), 2.77–2.64 (2H, m), 1.39 (3H, t), 1.34 (3H, t), 1.10 (3H, d) ppm.

LRMS (ESI): m/z [M+H]$^+$ 275, [M+Na]$^+$ 297.

Preparation 29

Ethyl 1-ethyl-5-{(2R)-2-[((2R)-2-[4-(benzyloxy)-3-(hydroxy methyl)phenyl]-2-{[tert-butyl(dimethyl)silyl]oxy}ethyl)amino]propyl}-1H-indole-2-carboxylate

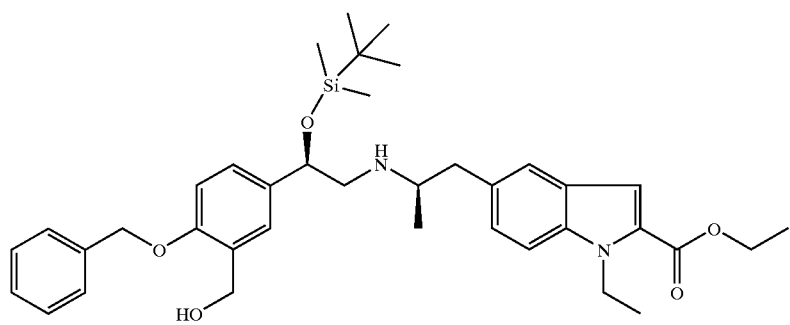

Prepared using the amine from Preparation 28, and the bromide from preparation 21 and the method described for Preparation 13.

$^1$H NMR (400 MHz, CD$_3$OD): δ=7.43–7.29 (8H, m), 7.19 (1H, s), 7.11 (1H, d), 6.99 (1H, d), 6.74 (1H, d), 5.00 (2H, s), 4.73–4.70 (1H, m), 4.61–4.56 (4H, m), 4.30 (2H, q), 3.00–2.88 (2H, m), 2.78–2.61 (3H, m), 1.37–1.31 (6H, m), 1.11 (3H, d), 0.73 (9H, s), –0.08 (3H, s), –0.24 (3H, s) ppm.

LRMS (ESI): m/z [M+H]$^+$ 645, [M+Na]$^+$ 667.

Preparation 30

Ethyl 1-ethyl-5-[(2R)-2-({(2R)-2-{[tert-butyl(dimethyl)silyl]oxy}-2-[4-hydroxy-3-(hydroxymethyl)phenyl]ethyl}amino)propyl]-1H-indole-2-carboxylate Prepared using the amine from Preparation 29 and the method described for Preparation 12.

$^1$H NMR (400 MHz, CD$_3$OD): δ=7.38–7.35 (2H, m), 7.19–7.09 (3H, m), 6.96 (1H, d), 6.64 (1H, d), 4.68–4.58 (5H, m), 4.37 (2H, q), 2.98–2.60 (5H, m), 1.41 (3H, t), 1.36 (3H, t), 1.10 (3H, d), 0.72 (9H, s), –0.09 (3H, s), –0.25 (3H, s), ppm.

LRMS (ESI): m/z [M+H]$^+$ 555, [M+Na]$^+$ 577.

Preparation 31

1-Ethyl-5-[(2R)-2-({(2R)-2-{[tert-butyl(dimethyl)silyl]oxy}-2-[4-hydroxy-3-(hydroxymethyl)phenyl]ethyl}amino)propyl]-1H-indole-2-carboxylic acid

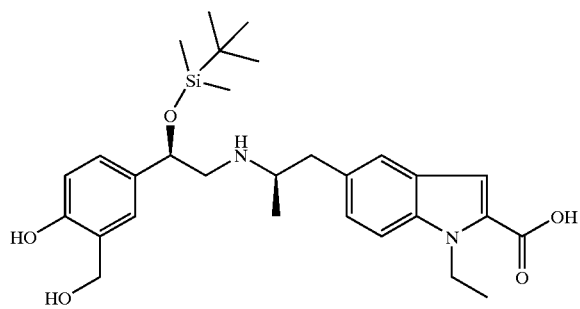

Prepared using the amine from Preparation 30 and the method described for Preparation 11.

¹H NMR (400 MHz, CD₃OD): δ=7.41–7.35 (2H, m), 7.21 (1H, bs), 7.07–6.95 (3H, m), 6.67 (1H, d), 4.94–4.91 (1H, m), 4.60–4.55 (4H, m), 3.54–3.49 (1H, m), 3.09–2.84 (4H, m), 1.27–1.21 (6H, m), 0.67 (9H, s), −0.09 (3H, s), −0.29 (3H, s), ppm.

LRMS (ESI): m/z [M+H]⁺ 527, [M+Na]⁺ 549.

Preparation 32

Acetic acid 1-methylene-propyl ester

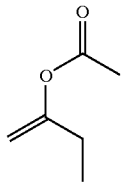

But-1-yne (13.5 g, 0.25 mol) was added to a solution of mercuric acetate (1.2 g, 4.6 mmol) and boron trifluoride dietherate (1.68 g, 11.8 mmol) in acetic anhydride (40 ml) at −10° C. After stirring for 3 h, the solution was left at −20° C. overnight. The reaction mixture was added to a cooled (0° C.) 6.6 M solution of sodium hydroxide (150 ml). Diethyl ether (150 ml) was then added and the mixture stirred for 1 h. The etheral layer was separated and washed with brine and dried (Na₂SO₄). The product was purified by distillation (120° C.) to yield a clear oil (4.5 g).

¹H NMR (400 MHz, CD₃OD): δ 1.05 (3H, t), 2.18 (3H, s), 2.20 (2H, q), 4.75 (2H, 2xs)

Preparation 33

1-tert-Butyl 2-methyl 5-(2-oxobutyl)-1H-indole-1,2-dicarboxylate

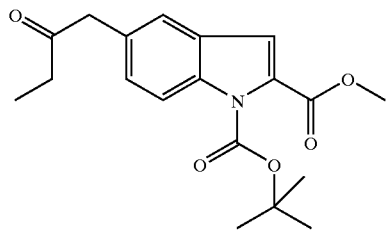

Prepared using the bromide from Preparation 18, the ester from preparation 32 and the method described for Preparation 17.

¹H NMR (400 MHz, CDCl₃): δ=8.03 (1H, d), 7.44 (1H, s), 7.25 (1H, d, partially obscured by solvent), 7.05 (1H, s), 3.92 (3H, s), 3.77 (2H, s), 2.48 (2H, q), 1.62 (9H, s), 1.03 (3H, t) ppm.

LRMS (ESI): m/z [M+Na]⁺ 368.

Preparation 34

Methyl 5-((2R)-2-{[(1R)-1-phenylethyl]amino}butyl)-1H-indole-2-carboxylate

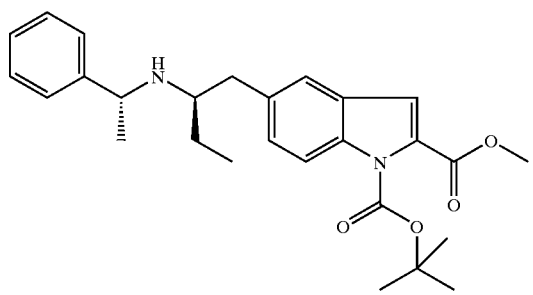

Prepared using the amine from Preparation 33 and the method described for Preparation 16.

¹H NMR (400 MHz, CD₃OD): δ=0.81–0.95 (3H, 2xt), 1.27 (3h, 2xd), 1.62 (9H, s), 2.53–2.89 (3H,m), 3.90 (1H, m), 3.92 (3H, 2xs), 6.82–7.20 (4H, m), 7.23–7.29 (4h, m), 7.90 (1H, m) ppm.

LRMS (APCI): m/z [M+H]⁺ 451.

Preparation 35

Methyl 5-((2R)-2-{[(1R)-1-phenylethyl]amino}butyl)-1H-indole-2-carboxylate

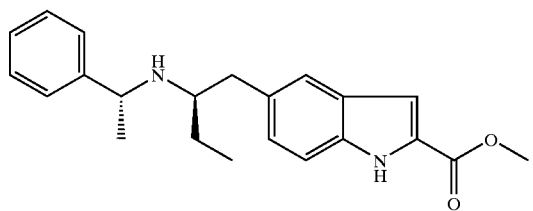

Prepared using the bromide from Preparation 34 and the method described for Preparation 15.

¹H NMR (400 MHz, CD₃OD): δ=7.50–7.41 (7H, m), 7.12 (1H, s), 7.03 (1H, d), 4.43 (1H, q), 3.91 (3H, s), 3.31–3.24 (2H, m), 3.15–3.08 (1H, m), 2.98–2.9 (1H, m), 1.67 (3H, d), 1.66–1.51 (1H, m), 0.9 (3H, t) ppm.

LRMS (ESI): m/z [M+H]⁺ 351.

Preparation 36

Methyl 5-[(2R)-2-aminobutyl]-1H-indole-2-carboxylate

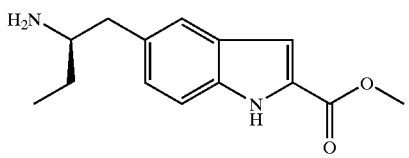

Prepared using the bromide from Preparation 35 and the method described for Preparation 14.

¹H NMR (400 MHz, CDCl₃): δ=9.39 (1H, bs), 7.49 (1H, s), 7.34 (1H, d), 7.13–7.15 (2H, m), 3.93 (3H, s), 2.99–2.88 (2H, m), 2.55–2.50 (1H, m), 1.51–1.20 (4H, m), 0.99 (3H, t) ppm.

LRMS (ESI): m/z [M+H]⁺ 247.

Preparation 37

Methyl 5-{(2R)-2-[((2R)-2-[4-(benzyloxy)-3-(hydroxymethyl)phenyl]-2-{[tert-butyl(dimethyl)silyl]oxy}ethyl)amino]butyl}-1H-indole-2-carboxylate

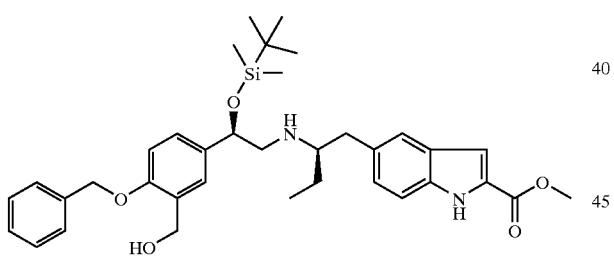

Prepared using the bromide from Preparation 18, the ester from preparation 36 and the method described for Preparation 13.

¹H NMR (400 MHz, CDCl₃): δ=8.83 (1H, bs), 7.60–7.50 (6H, m), 7.44 (1H, s), 7.41–7.26 (4H, m), 6.98 (1H, d), 5.25 (2H, s), 4.95–4.85 (3H, m), 4.08 (3H, s), 3.03–2.80 (5H, m), 1.95–1.55 (4H, m), 1.10 (3H, t), 1.01 (9H, s), 0.18 (3H, s), 0.00 (3H, s) ppm.

LRMS (ESI): m/z [M+H]⁺ 617.

Preparation 38

5-{(2R)-2-[((2R)-2-[4-(benzyloxy)-3-(hydroxymethyl)phenyl]-2-{[tert-butyl(dimethyl)silyl]oxy}ethyl)amino]butyl}-1H-indole-2-carboxylic acid

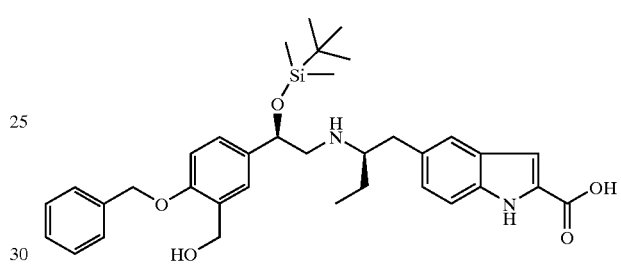

Preparation 37 (790 mg, 1.28 mmol) and LiOH (1 M in water, 2.56 ml) in THF (40 ml) and water (6 ml) were stirred at RT overnight. The solvent was removed in vacuo to yield a yellow foam (870 mg).

LRMS (APCI): m/z [M+H]⁺ 603.

Preparation 39

5-[(2R)-2-({(2R)-2-[4-(benzyloxy)-3-(hydroxymethyl)phenyl]-2-{[tert-butyl(dimethyl)silyl]oxy}-ethyl}amino)butyl]-N-(4-chlorobenzyl)-1H-indole-2-carboxamide

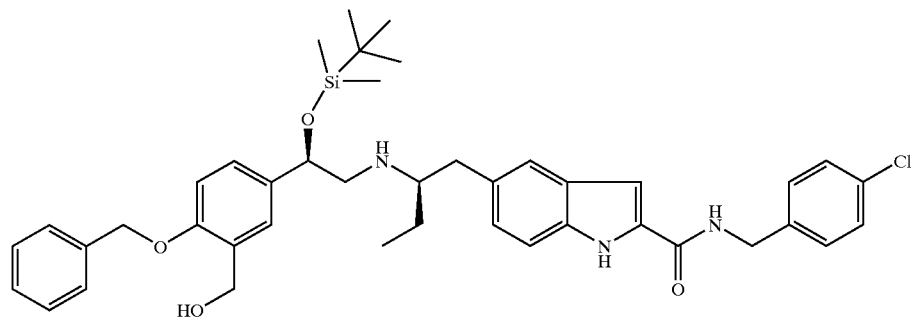

Prepared using the acid from Preparation 38 and the method described for Preparation 1.

¹H NMR (400 MHz, CD₃OD): δ=7.77–7.62 (12H, m), 7.38–7.34 (2H, m), 7.25 (1H, d), 6.99 (1H, d), 5.33 (2H, s), 5.01–5.05 (1H, m), 4.95 (2H, s), 4.85 (2H, s), 3.25–2.95 (5H, m), 2.00–1.65 (2H, m), 1.33 (3H, t), 1.10 (9H, s), 0.28 (3H, s), 0.10 (3H, s) ppm.

LRMS (ESI): m/z [M+H]⁺ 726.

Preparation 40

5-[(2R)-2-({(2R)-2-[4-(benzyloxy)-3-(hydroxymethyl)phenyl]-2-{[tert-butyl(dimethyl)silyl]oxy}-ethyl}amino)butyl]-N-(2-methoxybenzyl)-1H-indole-2-carboxamide

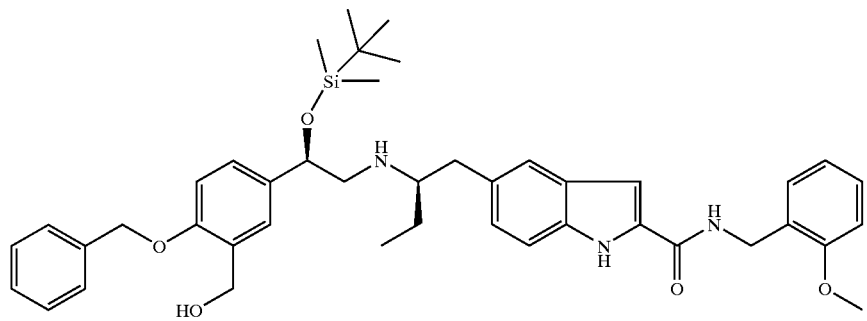

Prepared using the acid from Preparation 38 and the method described for Preparation 1.

¹H NMR (400 MHz, CD₃OD): δ=7.45–7.20 (10H, m), 7.10–6.85 (5H, m), 6.63 (1H, d), 5.00 (2H, s), 4.70 (1H, t), 4.60 (2H, d), 4.55 (2H, s), 3.85 (3H, s) 2.85 (1H, m), 2.75 (2H, m), 2.60 (2H, m), 1.60 (1H, m), 1.40 (1H, m), 1.00 (3H, t), 0.78 (9H, s), −0.05 (3H, s), −0.25 (3H, s).

LRMS (APCI): m/z [M+H]⁺ 722.

Preparation 41

5-[(2R)-2-({(2R)-2-[4-(benzyloxy)-3-(hydroxymethyl)phenyl]-2-{[tert-butyl(dimethyl)silyl]oxy}-ethyl]amino)butyl]-N-(2,6-dimethoxybenzyl)-1H-indole-2-carboxamide

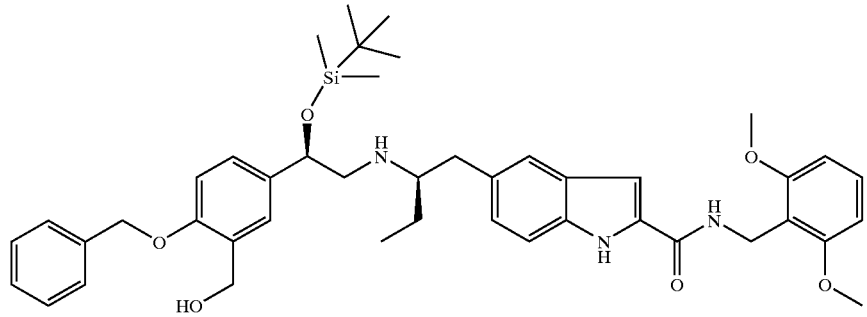

Prepared using the acid from Preparation 38 and the method described for Preparation 1.

¹H NMR (400 MHz, CD₃OD): Contains δ=7.50–7.20 (10H, m), 7.10–6.60 (4H, m), 6.50 (1H, m), 5.00 (2H, s), 4.70 (1H, t), 4.60 (2H, d), 4.55 (2H, s), 3.85 (6H, s), 2.85 (1H, m), 2.75 (2H, m), 2.60 (2H, m), 1.60 (1H, m), 1.40 (1H, m), 1.00 (3H, t), 0.78 (9H, s), −0.05 (3H, s), −0.25 (3H, s).

LRMS (APCI): m/z [M]⁺ 0.752.

Preparation 42

5-[(2R)-2-({(2R)-2-[4-(benzyloxy)-3-(hydroxymethyl)phenyl]-2-{[tert-butyl(dimethyl)silyl]oxy}-ethyl}amino)butyl]-N-(2-ethoxybenzyl)-1H-indole-2-carboxamide

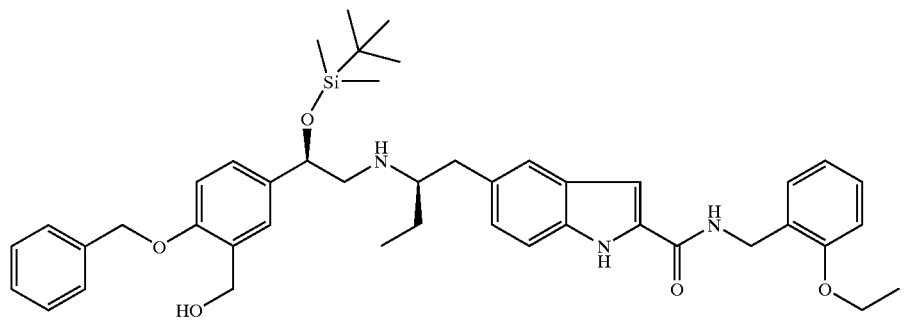

Prepared using the acid from Preparation 38 and the method described for Preparation 1.

$^1$H NMR (400 MHz, CD$_3$OD): δ=7.45–7.20 (10H, m), 7.10–6.80 (5H, m), 6.63 (1H, d), 4.98 (2H, s), 4.70 (1H, t), 4.60 (2H, d), 4.55 (2H, s), 4.08 (2H, q), 2.85 (1H, m), 2.75 (2H, m), 2.60 (2H, m), 1.60 (1H, m), 1.40 (4H, t, m), 0.98 (3H, t), 0.78 (9H, s), −0.05 (3H, s), −0.25 (3H, s).

LRMS (APCI): m/z [M+H]$^+$ 736.

Preparation 43

3-Methoxy-2-methylbenzamide

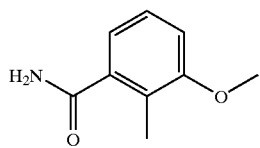

3-Methoxy-2-methylbenzoic acid (5.0 g, 30 mmol) in CH$_2$Cl$_2$ (90 ml) and DMF (90 ml) was treated with HOBt (4.06 g, 30 mmol) and WSCDI (5.75 g, 30 mmol) and the resulting mixture stirred at RT for 20 min. After cooling to 0° C. ammonia (2H in EtOH, 30 ml, 60 mmol) was added and the mixture stirred for a further 2 h. The mixture was filtered, the solvent was removed from the filtrate. The crude material was taken up in CH$_2$Cl$_2$ and washed with water and brine and dried (Na$_2$SO$_4$), which gave a white solid (2.9 g) on isolation.

$^1$H NMR (400 MHz, DMSO$_{d6}$): δ=7.62 (1H, s), 7.38 (1H, s), 7.18 (1H, t), 6.98(1H, d) 6.85 (1H, d), 3.80 (3H, s), 2.09 (3H, s).

Preparation 44

2-Methoxy-3-methylbenzamide

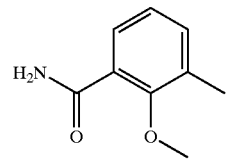

Prepared using 2-methoxy-3-methylbenzoic acid and the method described for Preparation 43.

$^1$H NMR (400 MHz, DMSO$_{d6}$): δ=7.62 (1H, s), 7.42 (1H, s), 7.40 (1H, d), 7.28 (1H, d), 7.01 (1H, t), 3.65 (3H, s), 2.20 (3H, s).

LRMS (ESI): m/z [M+Na]$^+$ 188.

Preparation 45

3-Methoxy-1-methylbenzamine

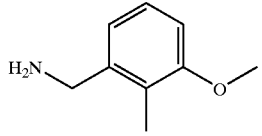

Preparation 44 (2.9 g, 17.5 mmol) in anhydrous THF (30 ml) was heated to 50° C. and BMS ("M in THF, 13 ml 26 mmol) was added dropwise over 40 min. The reaction was then heated to reflux for 4 h and then stirred overnight at RT. The reaction was quenched with 2M HCl (15 ml) and the pH adjusted to <3. The aqueous phase was washed with CH$_2$Cl$_2$ (×2) and then basified with 2M NaOH until ph>10. The product was extracted with CH$_2$Cl$_2$ (2×100 ml) and dried (Na$_2$SO$_4$). On isolation the compounds was a clear oil (506 mg).

$^1$H NMR (400 MHz, CDCl$_3$): δ 7.16 (1H,t), 6.90 (1H,d), 6.75(1H,d), 3.82 (2H, s), 3.80 (3H, s), 2.22 (3H, s), 1.80 (2H, bs)

LRMS (ESI): m/z [M+H]$^+$ 152.

Preparation 46

2-Methoxy-3-methylbenzamine

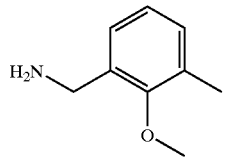

Prepared using Preparation 44 and the method described for Preparation 45.

$^1$H NMR (400 MHz, CDCl$_3$): δ 7.22 (1H, d), 7.20 (1H, d), 6.96(1H, t), 3.90 (2H, s), 3.78 (3H, s), 2.81 (NH2), 2.32 (3H, s)

LRMS (ESI): m/z [M+H]$^+$ 152

Preparation 47

4-Benzyloxy-2,6-dimethoxybenzaldehyde

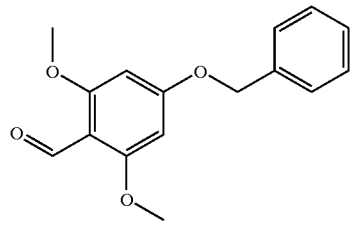

2-6-Dimethoxy-4-hydroxybenzaldehyde (1.83 g, 10 mmol), benzyl bromide (1.71 g, 10 mmol) and anhydrous K$_2$CO$_3$ (2.76 g, 20 mmol) in acetonitrile (25 ml) were heated to reflux for 4 h. The reaction mixture was diluted with EtOAc (50 ml) and washed with water (50 ml), brine (50 l) and dried (MgSO$_4$). The crude material was purified by chromatography (0–75% EtOAc in heptane) to give an off-white colour solid (2.11 g).

$^1$H NMR (400 MHz, CDCl$_3$): δ 3.86 (6H, s), 5.12 (2H, s), 6.16 (2H, s), 7.37–7.45 (5H, m), 10.36 (1H, s)

LRMS (ESI): m/z [M+H]$^+$ 273, [M+Na]$^+$ 295

Preparation 48

Allyl-(4-benzyloxy-2,6-dimethoxybenzyl)amine

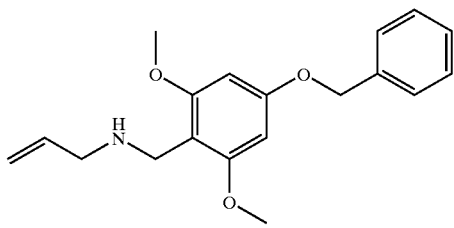

Preparation 47 (1.0 g, 3.68 mmol), allylamine (210 mg, 7.35 mmol), sodium triacetoxyborohydride (779 mg, 7.35 mmol) were stirred at RT in CH$_2$Cl$_2$ (25 ml) 16 h. The mixture was diluted with CH$_2$Cl$_2$ (50 ml), washed with sat. Na$_2$CO$_3$ (2×50 ml), brine (50 ml) and dried (MgSO$_4$). The product was purified by chromatography (0–5% MeOH in CH$_2$Cl$_2$ with 1% NH$_3$) to yield a yellow oil (1.03 g).

$^1$H NMR (400 MHz, CDCl$_3$): δ 1.39 (1H, bs), 3.23 (2H, d), 3.78 (6H, s), 3.82 (2H, s), 5.06 (2H, s), 5.13 (2H, dd), 5.95 (1H, m), 6.20 (2H, s), 7.23–7.45 (5H, m)

LRMS (ESI): m/z [M+H]$^+$ 314.

Preparation 49

4-Benzyloxy-2,6-dimethoxybenzylamine

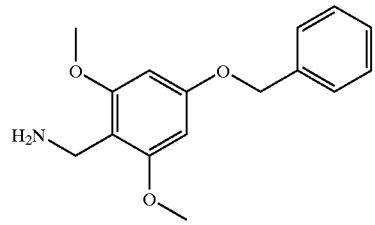

Preparation 48 (500 mg, 1.60 mmol) in CH$_2$Cl$_2$ (5 ml) was added to a solution of tetrakis(triphenylphosphine) palladium(0) (20 mg, 1.60 mmol) and N,N'-dimethylbarbituric acid (750 mg, 4.79 (mmol) in CH$_2$Cl$_2$ (15 ml) and the mixture heated to 35° C. for 4 h. The mixture was diluted with CH$_2$Cl$_2$ (20 ml) and washed with sat. Na$_2$CO$_3$ (2×20 ml) and brine (20 ml) and dried, (MgSO$_4$) to leave a yellow oil (529 mg).

LRMS (ESI): m/z [M+Na]$^+$ 396.

Preparation 50

2-Hydroxy-6-methoxybenzamide

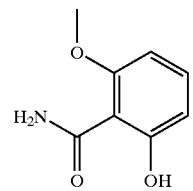

2-hydroxy-6-methoxybenzoic acid (4.0 g, 23.81 mmol) thionyl chloride (10 ml) and DMF (1 drop) were heated to reflux for 2 h. The solvents were removed in vacuo and the material taken up in CH$_2$Cl$_2$ (25 ml) and cooled <0° C. 0.88 Ammonia (3 ml) was added dropwise over 5 min to the mixture and the reaction stirred overnight at RT. The reaction was diluted with CH$_2$Cl$_2$ (incorporating 2% MeOH) and acidified to pH 2 with 10% HCl solution, the organics were washed with water and the solvent removed. The crude material was partially purified by chromatography (0–100% EtOAc in heptane) to leave a white solid (1.54 g).

$^1$H NMR (400 MHz, DMSO$_{d6}$): δ 3.87 (3H, s), 6.45 (1H, dd), 6.52 (1H, dd), 7.30 (1H, t), 8.10 (1H, bs), 8.16 (1H, bs).

LRMS (ESI): m/z [M+H]$^+$ 168.

Preparation 51

2-benzyloxy-6-methoxybenzamide

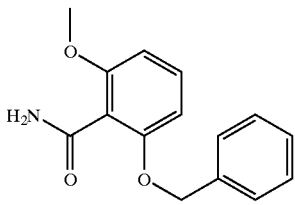

Prepared using Preparation 50 and the method described for Preparation 47.

$^1$H NMR (400 MHz, CDCl$_3$): δ 3.85 (3H, s), 5.12 (2H, s), 5.76 (2H, bs), 6.59 (1H, d), 6.61 (1H, d), 7.28–7.43 (5H, m).

LRMS (ESI): m/z [M+H]$^+$ 258.

Preparation 52

4-Benzyloxy-2,6-dimethoxybenzaldehyde

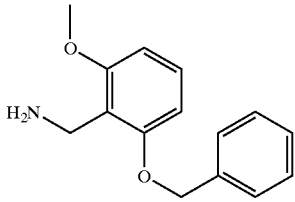

Lithium aluminiumhydride (1M in Et$_2$O, 5.21 ml, 5.21 mmol) was added to a solution of Preparation 51 (1.34 g, 5.21 mmol) in THF (20 ml) and the mixture heated to 40° C. for 6 h. The reaction was quenched with (1 M NaOH (2 ml) and the mixture stirred at RT for 1 h. The product was extracted with EtOAc (2×30 ml) and the organics washed with water (50 ml), brine (50 ml) and dried (MgSO$_4$). The product was purified by chromatography (0–5% MeOH in CH$_2$Cl$_2$ With 1% NH$_3$) to yield a yellow oil (315 mg).

$^1$H NMR (400 MHz, CDCl$_3$): δ 1.73 (2H, bs), 3.84 (3H, s), 3.90 (1H, s), 5.09 (2H, s), 6.57 (1H, d), 6.61 (1H, d), 7.16 (1H, dd), 7.32–7.44 (5H, m).

LRMS (ESI): m/z [M+H]$^+$ 244.

Preparation 53

Methyl 3-bromo-2,6-dimethoxybenzoate

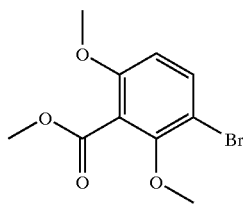

3-Bromo-2,6-dimethoxybenzoic acid (5.0 g, 19.2 mmol) and thionyl chloride (10 ml) were heated to reflux for 2 h. The mixture was then concentrated in vacuo and diluted with CH$_2$Cl$_2$ (20 ml) and added to a solution of MeOH (614 mg, 38.4 mmol) and triethylamine (3.88 g, 38.4 mmol) in CH$_2$Cl$_2$ (100 ml) at 0° C. The resulting mixture was allowed to warm to RT and stirred for 64 h. The organics were washed with 10% HCl (50 ml), brine (50 ml) and dried (MgSO$_4$) and purified by chromatography (0–50% EtOAC in heptane) to leave a white solid (4.17 g).

$^1$H NMR (400 MHz, CDCl$_3$): δ 3.82 (3H, s), 3.88 (3H, s), 3.93 (3H, s), 6.61 (1H, d), 7.51 (1H, d).

LRMS (ESI): m/z [M+Na]$^+$ 299/297.

Preparation 54

Methyl 2,6-dimethoxy-3-hydroxybenzoate

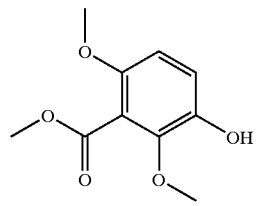

Preparation 53 (4.16 g 15.1 mmol) in THF (100 ml) was cooled to −78° C. under nitrogen and treated with butyl-lithium (1.6 M in hexanes, 10.4 ml, 16.6 mmol). After 10 min at this temp. triisopropylborate (5.69 g, 20.3 mmol) was added and the mixture allowed to warm to RT over 1 h and stirred for a further 2 h. The reaction was quenched with 2M HCl (20 ml) and the solution stirred at RT for 20 h. The product was extracted with EtOAc (2×100 ml), washed with brine (100 ml) and dried (MgSO$_4$) to leave a brown oil (3.80 g). The crude material was diluted with THF (20 ml) and hydrogen peroxide (100 vol., 4 ml) and the resulting mixture heated to reflux for 20 h. EtOAc (50 ml) was added and the organics washed with 10% ammonium iron (III) sulfate until no more colour change, then washed with brine (50 ml) before being dried (MgSO$_4$). The product was purified by chromatography (0–50% EtOAc in heptane) (1.03 g).

$^1$H NMR (400 MHz, CDCl$_3$): δ 3.78 (3H, s), 3.89 (3H, s), 3.95 (3H, s), 6.60 (1H, d), 6.95 (1H, d), 5.07 (1H, bs).

LRMS (ESI): m/z [M+Na]$^+$ 235.

Preparation 55

Methyl 3-benzyloxy-2,6-dimethoxybenzoate

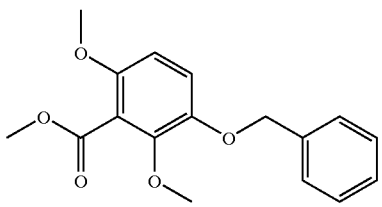

Prepared using Preparation 54 and the method described for Preparation 47.

$^1$H NMR (400 MHz, CDCl$_3$): δ 3.78 (3H, s), 3.92 (3H, s), 3.93 (3H, s), 5.08 (2H, s), 6.57 (1H, d), 6.90 (1H, d), 7.28–7.42 (5H, m)

LRMS (ESI): m/z [M+Na]$^+$ 325.

Preparation 56

3-Benzyloxy-2,6-dimethoxybenzoic acid

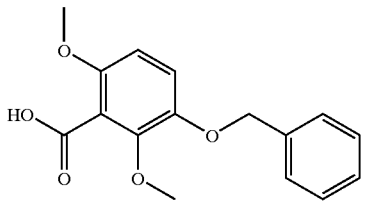

Preparation 55 (870 mg, 2.89 mmol) and NaOH (230 mg, 5.76 mmol) in a mixture of THF (10 ml) and water (2 ml) were heated to reflux for 2 days. The solvent was removed and the material acidified to pH 2 with 10% HCl. The acid was extracted with EtOAc (100 ml) and washed with brine (100 ml) and dried (MgSO$_4$). The resulting solids were slurried in hexane and filtered to leave a cream colour solid (536 mg).

$^1$H NMR (400 MHz, DMSO$_{d6}$): δ 3.69 (3H, s), 3.75 (3H, s), 5.08 (2H, s), 6.70 (1H, d), 7.07 (1H, d), 7.29–7.45 (5H, m).

LRMS (ESI): m/z [M−H]$^-$ 287.

Preparation 57

3-Benzyloxy-2,6-dimethoxybenzamide

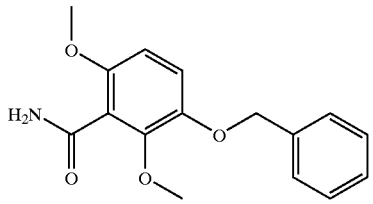

Prepared using Preparation 56 and the method described for Preparation 1.

$^1$H NMR (400 MHz, DMSO$_{d6}$): δ 3.67 (3H, s), 3.75 (3H, s), 5.06 (2H, s), 6.66 (1H, d), 7.02 (1H, d), 7.31–7.46 (5H, m), 7.25 (1H, bs), 7.56 (1H, bs).

LRMS (ESI): m/z [M+Na]$^+$ 310.

Preparation 58

(3-Benzyloxy-2,6-dimethoxy-benzyl)-carbamic acid tert-butyl ester

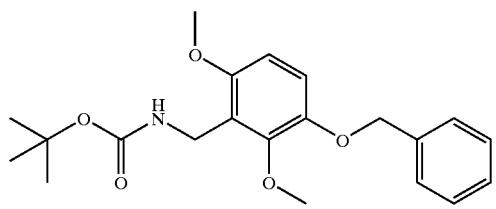

Preparation 57 (277 mg, 965 μmol) and BMS (2M in THF, 0.97 ml, 1.93 mmol) in THF (10 ml) were heated to reflux for 20 min. MeOH (5 ml) was added followed by cHCl (0.2 ml) and the resulting mixture heated for a further 1 h. The solvents were removed and the crude product triturated with Et$_2$O to leave a white solid (277 mg). This solid was taken up in a mixture of dioxane (10 ml) and water (1 ml) and treated with di-tert-butyloxydicarbonate (325 mg, 10.6 mmol) and sodium hydrogen carbonate (162 mg, 10.6 mmol) and the resulting mixture stirred at RT for 4 h. The mixture was diluted with EtOAc (25 ml) and washed with brine (50 ml) and dried (MgSO$_4$) to leave a light brown coloured oil (427 mg). This crude material was taken up in acetone (10 ml) and treated with iodomethane (71 mg, 500 μmol) and anhydrous potassium carbonate (266 mg, 1.93 mmol) and heated to reflux for 16 h. A further aliquot of iodomethane (71 mg, 500 μmol) was added and heating continued for a further 2 h. The reaction was quenched with water (20 ml) and the product extracted with EtOAc (2×50 ml). The organics were washed with brine and dried (MgSO$_4$) and the crude material purified by chromatography (0–30% EtOAc in heptane) to yield a clear oil (212 mg).

$^1$H NMR (400 MHz, CDCl$_3$): δ 1.44 (9H, s), 3.79 (3H, s), 3.91 (3H, s), 4.42 (2H, d), 5.05 (3H, s), 6.52 (1H, d), 6.83 (1H, d), 7.31–7.45 (5H, m).

LRMS (ESI): m/z [M+Na]$^+$ 396.

Preparation 59

3-Benzyloxy-2,6-dimethoxybenzylamie hydrochloride

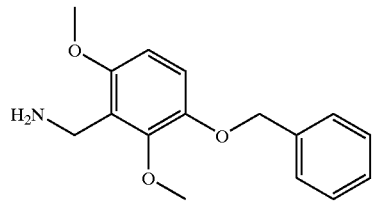

Preparation 58 (212 mg, 568 μmol) in dioxane (5 ml) was treated with HCl (4M in dioxane, 1.0 ml) and the solution stirred at RT for 2 h and at 60° C. for 2 h. the solvent was removed in vacuo to yield a white solid (160 mg).

$^1$H NMR (400 MHz, DMSO$_{d6}$): δ 3.76 (3H, s), 3.83 (3H, s), 3.93 (2H, bs), 5.09 (2H, s), 6.74 (1H, d), 7.13 (1H, d), 7.32–7.46 (5H, m), 7.98 (3H, bs).

LRMS (ESI): m/z [M+H]$^+$ 274.

In vitro Activity of the Indole Derivatives of Formula (1)

The ability of the indole derivatives of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-Pig Trachea

Male, Dunkin-Hartley guinea pigs (475–525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3–4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 μM Indomethacin (Sigma 17378), 10 μM Guanethidine (Sigma G8520) and 10 μM Atenolol (Sigma A7655), heated at 37° C. and gassed with 95% O$_2$/5% CO$_2$, before applying an initial tension of 1 g. The preparations are allowed to equilibrate for a further 30–45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma 15627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^{e}/3^{e-6}$ M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The $EC_{50}$ value for beta-2 agonist according to the present invention refers to the concentration of compound required to produce half maximal effect. Data for beta-2 agonists according to the present invention are then expressed as relative potency to isoprenaline defined by the ratio ($EC_{50}$ beta-2 agonist)/(EC50 Isoprenaline).

Confirmation of Beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective $\beta_2$ antagonist) which results in the case of a beta-2 mediated effect in a rightward-shift of the test compound dose response curve. It has thus been found that the indole derivatives of formula (1) according to the present invention that have been tested show a relative potency to Isoprenaline which is comprised between 0.008 and 2.0.

According to another alternative, the agonist potency for the β2 receptor of the indole derivatives of the formula (1) may also be determined by the measure of the concentration of compound according to the present invention required to produce half maximal effect ($EC_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, 1–5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46–50, 1987 and Bouvier et al., Mol Pharmacol 33: 133–139 1988 CHOhβ2) were grown in Dulbeccos MEM/NUT MIX F12 (Gibco, 21331–020) supplemented with 10% foetal bovine serum (Sigma, F4135, Lot 90K8404 Exp 09/04), 2 mM glutamine (Sigma, G7513), 500 µg/ml geneticin (Sigma, G7034) and 10 µg/ml puromycin (Sigma, P8833). Cells were seeded to give about 90% confluency for testing.

Assay Method

25 µl/well each dose of compound was transferred into a cAMP-Flashplate® (NEN, SMP004B), with 1% DMSO as basal controls and 100 nM Isoprenaline as max controls. This was diluted 1:2 by the addition of 25 µl/well PBS. Cells were trypsinised (0.25% Sigma, T4049), washed with PBS (Gibco, 14040–174) and resuspended in stimulation buffer (NEN, SMP004B) to give $1\times10^6$ cells/ml CHOhB2. Compounds were incubated with 50 µl/well cells for 1 hour. Cells were then lysed by the addition of 100 µl/well detection buffer (NEN, SMP004B) containing 0.18 µCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit.

It has thus been found that the indole derivatives of formula (1) according to the present invention that are illustrated in examples 1 to 36 above show a β2 cAMP $EC_{50}$ between 0.02 nM and 4 nM.

The below results illustrate the activity of the compounds of formula (1):

| Example Number | Cell based cAMP β2 activity (nM) |
|---|---|
| 1 | 0.02 |
| 2 | 0.80 |
| 3 | 0.05 |
| 4 | 0.12 |
| 9 | 0.02 |
| 22 | 0.02 |
| 29 | 3.99 |
| 36 | 0.38 |

What is claimed is:
1. A compound of the formula (1):

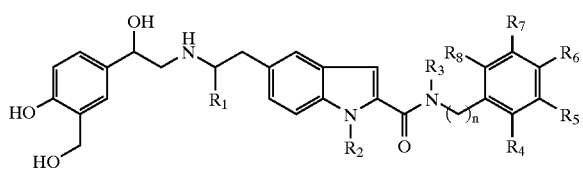

(1)

wherein
n is 0, 1, 2, 3 or 4;
$R_1$ and $R_2$ are each independently selected from hydrogen and $(C_1–C_4)$alkyl;
$R_3$ is selected from the group consisting of hydrogen and $(C_1–C_6)$alkyl optionally substituted by a hydroxy; and R$_4$, R$_5$, R$_6$, R$_7$ and R$_8$ are each independently selected from the group consisting of hydrogen, hydroxy, (C$_1$–C$_6$)alkyl, (C$_1$–C$_6$)alkoxy, benzyloxy, hydroxy (C$_1$–C$_6$)alkyl, thio(C$_1$–C$_6$)alkyl, halo and trifluoromethyl;

or a pharmaceutically acceptable salt and/or isomer, tautomer, solvate or isotopic variation thereof.

2. A compound according to claim 1 wherein n is 1 or 2;

R$_1$ is a (C$_1$–C$_4$)alkyl; and

R$_3$ is selected from hydrogen and (C$_1$–C$_6$)alkyl;

or a pharmaceutically acceptable salt and/or isomer, tautomer, solvate or isotopic variation thereof.

3. A compound according to claim 1 wherein n is 1 or 2;

R$_1$ is selected from methyl and ethyl;

R$_2$ is selected from hydrogen, methyl and ethyl; and

R$_3$ is selected from hydrogen and methyl;

or a pharmaceutically acceptable salt and/or isomer, tautomer, solvate or isotopic variation thereof.

4. A compound according to claim 1 wherein n is 1 or 2;

R$_1$ is selected from methyl and ethyl;

R$_2$ is selected from hydrogen, methyl and ethyl;

R$_3$ is selected from hydrogen and methyl; and

R$_4$, R$_5$, R$_6$, R$_7$ and R$_8$ are each independently selected from the group consisting of hydrogen, hydroxy, methyl, methoxy, ethoxy, benzyloxy, thiomethyl, halo and trifluoromethyl;

or a pharmaceutically acceptable salt and/or isomer, tautomer, solvate or isotopic variation thereof.

5. A compound according to any one of claims 1 to 4, wherein at least two of R$_4$, R$_5$, R$_6$, R$_7$ and R$_8$ are hydrogen.

6. A compound according to claim 1 wherein n is 1 or 2; R$_1$ is methyl; R$_2$ and R$_3$ are hydrogen; and R$_4$, R$_5$, R$_6$, R$_7$ and R$_8$ are each independently selected from the group consisting of hydrogen, hydroxy, (C$_1$–C$_6$)alkyl, (C$_1$–C$_6$)alkoxy, hydroxy(C$_1$–C$_6$)alkyl, thio(C$_1$–C$_6$)alkyl, halo and trifluoromethyl;

or a pharmaceutically acceptable salt and/or isomer, tautomer, solvate or isotopic variation thereof.

7. A compound according to claim 1 wherein n is 1; R$_1$ is methyl; R$_2$ and R$_3$ are hydrogen; and R$_4$, R$_5$, R$_6$, R$_7$ and R$_8$ are each independently selected from the group consisting of hydrogen, hydroxy, (C$_1$–C$_6$)alkyl, (C$_1$–C$_6$)alkoxy, thio (C$_1$–C$_6$)alkyl and trifluoromethyl;

or a pharmaceutically acceptable salt and/or isomer, tautomer, solvate or isotopic variation thereof.

8. A compound according to claim 1 wherein n is 1; R$_1$ is methyl; R$_2$ and R$_3$ are hydrogen; and R$_4$, R$_5$, R$_6$, R$_7$ and R$_8$ are each independently selected from the group consisting of hydrogen, (C$_1$–C$_6$)alkyl, (C$_1$–C$_6$)alkoxy and trifluoromethyl; provided that at least two of R$_4$, R$_5$, R$_6$, R$_7$ and R$_8$ are hydrogen;

or a pharmaceutically acceptable salt and/or isomer, tautomer, solvate or isotopic variation thereof.

9. A compound according to claim 1 wherein n is 1; R$_1$ is methyl; R$_2$ and R$_3$ are hydrogen; and R$_4$, R$_5$, R$_6$, R$_7$ and R$_8$ are each independently selected from the group consisting of hydrogen, methyl, methoxy and trifluoromethyl; provided that at least two of R$_4$, R$_5$, R$_6$, R$_7$ and R$_8$ are hydrogen;

or a pharmaceutically acceptable salt and/or isomer, tautomer, solvate or isotopic variation thereof.

10. A compound according to claim 1 selected from the group consisting of:

5-[(2R)-2-({(2R)-2-hydroxy-2-[4-hydroxy-3-(hydroxymethyl)phenyl]ethyl}amino)propyl]-N-(2-methoxybenzyl)-1H-indole-2-carboxamide, 5-[(2R)-2-({(2R)-2-hydroxy-2-[4-hydroxy-3-(hydroxymethyl)phenyl]ethyl}amino)propyl]-N-[4-(trifluoromethyl)benzyl]-1H-indole-2-carboxamide, N-(2,6-dimethoxybenzyl)-5-[(2R)-2-({(2R)-2-hydroxy-2-[4-hydroxy-3-(hydroxymethyl)phenyl]ethyl}amino) propyl]-1H-indole-2-carboxamide, 5-[(2R)-2-({(2R)-2-hydroxy-2-[4-hydroxy-3-(hydroxymethyl)phenyl]ethyl}amino)propyl]-N-(3-methoxybenzyl)-1H-indole-2-carboxamide, 5-[(2R)-2-({(2R)-2-hydroxy-2-[4-hydroxy-3-(hydroxymethyl)phenyl]ethyl}amino)propyl]-N-[2-(3-methoxyphenyl)ethyl]-1H-indole-2-carboxamide, 5-[(2R)-2-({(2R)-2-Hydroxy-2-(4-hydroxy-3-hydroxymethyl phenyl)ethyl}amino)propyl}-N-(2,4-dichlorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(3-hydroxy-2,6-dimethoxybenzyl)-1H-indole-2-carboxamide, 5-[(2R)-2-({(2R)-2-Hydroxy-2-(4-benzyloxy-3-hydroxy methyl phenyl)ethyl} amino)propyl}-N-(2-benzyloxy-6-methoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(4-hydroxy-2,6-dimethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-benzyloxy-6-methoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-hydroxy-6-methoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2,6-difluorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-chlorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-fluorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(4-hydroxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(3-hydroxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-methylsulfanylbenzyl)-1H-indole-2-carboxamide, 5-[(2R)-2-({(2R)-2-Hydroxy-2-(4-hydroxy-3-hydroxymethyl phenyl)ethyl}amino)propyl}-N-(4-methylsulfanylbenzyl)-1H-indole-2-carboxamide, 5-[(2R)-2-({(2R)-2-Hydroxy-2-(4-hydroxy-3-hydroxymethyl phenyl)ethyl}amino)propyl}-N-(2,3-dimethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2,4-dimethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-ethoxybenzyl)-1H-indole-2-carboxamide, 5-[(2R)-2-({(2R)-2-Hydroxy-2-(4-hydroxy-3-hydroxymethyl phenyl)ethyl}amino)propyl}-N-benzyl-N-methyl-1H-indole-2-carboxamide,

[(2R)-2-({(2R)-2-Hydroxy-2-(4-hydroxy-3-hydroxymethyl phenyl)ethyl}amino)propyl}-N-benzyl-1H-indole-2-carboxamide,

[(2R)-2-({(2R)-2-Hydroxy-2-(4-hydroxy-3-hydroxymethyl phenyl)ethyl}amino)propyl}-N-(4-fluorobenzyl)-1H-indole-2-carboxamide, 5-[(2R)-2-({(2R)-2-Hydroxy-2-(4-hydroxy-3-hydroxymethyl phenyl)ethyl}amino)propyl}-N-(2-methoxy-3-methyl-benzyl)-1H-indole-2-carboxamide, 5-[(2R)-2-({(2R)-2-Hydroxy-2-(4-hydroxy-3-hydroxymethyl phenyl)ethyl}amino)propyl}-N-(3-methoxy-2-methylbenzyl)-1H-indole-2-carboxamide, 1-Ethyl-5-[(2R)-2-({(2R)-2-hydroxy-2-(4-hydroxy-3-hydroxy methylphenyl)ethyl}amino)propyl}-N-(2,6-dimethoxybenzyl)-1H-indole-2-carboxamide, 1-Ethyl-5-[(2R)-2-({(2R)-2-hydroxy-2-(4-hydroxy-3-hydroxy methylphenyl)ethyl}amino)propyl}-N-(2-ethoxybenzyl)-1H-indole-2-carboxamide, 1-Ethyl-5-[(2R)-2-({(2R)-2-hydroxy-2-(4-hydroxy-3-hydroxy methylphenyl)ethyl}amino)propyl}-N-(4-chlorobenzyl)-1H-indole-2-carboxamide, 1-Methyl-5-[(2R)-2-({(2R)-2-hydroxy-2-(4-hydroxy-3-hydroxy methylphenyl)ethyl}amino)propyl}-N-(2,6-dimethoxybenzyl)-1H-indole-2-carboxamide, 1-Methyl-5-[(2R)-2-({(2R)-2-hydroxy-2-(4-hydroxy-3-hydroxy methylphenyl)ethyl}amino)propyl}-N-(2-methoxybenzyl)-1H-indole-2-carboxamide, 1-Methyl-5-[(2R)-2-({(2R)-2-hydroxy-2-(4-hydroxy-3-hydroxy methylphenyl)ethyl}amino)propyl}-N-(4-chlorobenzyl)-1H-indole-2-carboxamide, 5-[(2R)-2-({(2R)-2-Hydroxy-2-(4-hydroxy-3-hydroxymethyl phenyl)ethyl}amino)butyl}-N-(2-methoxybenzyl)-1H-indole-2-carboxamide, 5-[(2R)-2-({(2R)-2-Hydroxy-2-(4-hydroxy-3-hydroxymethyl phenyl)ethyl}amino)butyl}-N-(2,6-dimethoxybenzyl)-1H-indole-2-carboxamide, 5-[(2R)-2-({(2R)-2-Hydroxy-2-(4-hydroxy-3-hydroxymethyl phenyl)ethyl}amino)butyl}-N-(2-ethoxybenzyl)-1H-indole-2-carboxamide, and, 5-[(2R)-2-({(2R)-2-Hydroxy-2-(4-hydroxy-3-hydroxymethyl phenyl)ethyl}amino)butyl}-N-benzyl-1H-indole-2-carboxamide.

11. A pharmaceutical composition comprising a compound of claim 1 or a pharmaceutically acceptable salt or derived form thereof, together with pharmaceutically acceptable excipients and/or additives.

* * * * *